(12) United States Patent
Marx et al.

(10) Patent No.: US 8,257,981 B2
(45) Date of Patent: Sep. 4, 2012

(54) LANTHANIDE CHELATES AND USE THEREOF IN BIOANALYSIS

(75) Inventors: Jörg Marx, Heidelausiger Weg (DE); Frank Schumer, Czermaks Garten (DE); Regina Lischewski, Dorfstrasse (DE); Kornelia Zeckert, Rosslauer Strasse (DE); Hans-Joachim Böhme, Froschweg (DE); Horst Hennig, Johannisallee (DE)

(73) Assignee: Sensient Imaging Technologies GmbH, Wolfen (DE)

( * ) Notice: Subject to any disclaimer, the term of this patent is extended or adjusted under 35 U.S.C. 154(b) by 1215 days.

(21) Appl. No.: 11/568,396

(22) PCT Filed: Apr. 30, 2005

(86) PCT No.: PCT/DE2005/000804
§ 371 (c)(1),
(2), (4) Date: Nov. 7, 2007

(87) PCT Pub. No.: WO2005/108405
PCT Pub. Date: Nov. 17, 2005

(65) Prior Publication Data
US 2011/0136242 A1    Jun. 9, 2011

(30) Foreign Application Priority Data
May 7, 2004 (DE) .......................... 10 2004 022 628

(51) Int. Cl.
G01N 21/76 (2006.01)
(52) U.S. Cl. .............. 436/172; 436/71; 436/81; 436/82; 436/86; 436/94; 436/87; 564/305; 546/88; 546/89; 546/181; 549/390; 549/401
(58) Field of Classification Search .................. 564/305; 436/172, 71, 81, 82, 86, 94, 87; 546/88, 546/89, 181; 549/390, 401
See application file for complete search history.

(56) References Cited

U.S. PATENT DOCUMENTS

| | | |
|---|---|---|
| 4,808,541 A | 2/1989 | Mikola et al. |
| 4,920,195 A | 4/1990 | Kankare et al. |
| 5,032,677 A | 7/1991 | Hale et al. |

FOREIGN PATENT DOCUMENTS

| | | |
|---|---|---|
| WO | 00/01663 | 1/2000 |
| WO | 03/035655 | 5/2003 |

OTHER PUBLICATIONS

Japanese Patent Office Action for Application No. 2007-511846 dated May 27, 2011 (6 pages).
Korean Patent Office Action for Application No. 10-2006-7025716 dated Oct. 11, 2011 (6 pages) with English translation.

*Primary Examiner* — Jill Warden
*Assistant Examiner* — Monique Cole
(74) *Attorney, Agent, or Firm* — Michael Best & Friedrich LLP

(57) ABSTRACT

Novel chemical compounds, with application in fluorometric analytical methods, for qualitative and quantitative determination of biomolecules. The aim of the invention is to identify and prove the suitability of such compounds. Said aim is achieved with compounds of formula (1) where $R^1$ is an antenna function, $R^2$ is a chelate forming agent, containing a coordinated lanthanide(III)ion, X is —OH or a group with affinity for the biomolecule, bonded to a carboxylate group of the chelate forming agent by means of an amide bond and Y is —H or a group with affinity for the biomolecule, coupled to the antenna function.

17 Claims, 6 Drawing Sheets

LANTHANIDE CHELATES AND USE THEREOF IN BIOANALYSIS

CROSS-REFERENCE TO RELATED APPLICATIONS

This patent application is a national stage filing under 35 U.S.C. 371 of International Application No. PCT/DE2005/000804, filed 30 Apr. 2005, which claims foreign priority to German Patent Application No. 10 2004 022 628.8, filed 7 May 2004, the disclosures of which are incorporated by reference herein in their entireties. Priority to each application is hereby claimed.

BACKGROUND OF THE INVENTION

The invention relates to lanthanide chelates, their manufacture and characterization and their use in bioanalysis, preferably in fluorescence spectroscopy.

Using lanthanide complexes in fluorescence spectroscopy is already known. U.S. Pat. No. 4,374,120 describes Eu and Tb chelates as fluorescent markers with a relatively long fluorescent time of 50 to 1000 microseconds, ligands are aminopolycarboxylic acids, among other things. In addition, it is also known that some lanthanide fluorescence chelate complexes are particularly suited for time-resolved fluorimetry, wherein TB (III)-BPTA—NHS and Eu(III) estrogen are preferred and the former is used in a DNA hybridization assay (K. Matsumoto et al., RIKEN Review 35, May 2001). Lanthanide chelates are used according to WO 00/01663 in HTRF (homogenous time-resolved fluorescence) assays. Using cyanine and indocyanine dyes in biomedicine is known (U.S. Pat. No. 6,217,848, U.S. Pat. No. 6,190,641 with additional evidence). DE 42 22 255 describes marking reagents with a lanthanide ion chelating structure for use in gene probe diagnostics. Preferred as a lanthanide ion chelating structure are pyridine derivates, spacers are polyalkyl amine and polyethylene glycol, and furocumarin derivates are photosensitive. In an article in the Journal of Alloys and Compounds 1995, 225, 511-14 on Page 112, H. Takalo et al. describe Tb(III) and Eu(III) chelates and their luminescence yield. To determine phosphorylation activities, cryptates are used in DE 698 13 850, which contain a rare earth molecule such as TB, Eu, Sm, Dy, Nd, a complexing agent like bispyridine and which are used as the fluorescent donor bond. I. Hemmilää and S. Webb describe principles of time-resolved fluorimetry TRF with lanthanide chelates for drug screening in DDT, 1997, 2, 373-381. A sensor for detecting nucleic acids that uses rare earth dyes as fluorophores in a preferred embodiment is described in DE 102 59 677.

For use in bioanalysis by measuring the energy transfer of a donor to an acceptor, it is necessary to have compounds available that are capable of this transfer of energy. One possibility is fluorescence resonance energy transfer (FRET) as a special form of energy transfer, which is based on an interaction of two spatially separated dipoles, one of which (donor) is electronically excited. If both dipoles are in resonance with one another, the excitation energy of the fluorescent donor can be transferred nonradiatively to an acceptor. Because of its high sensitivity and the strong dependence on the distance between the donor and acceptor, FRET has found wide-ranging application in the identification and characterization of biologically relevant substrates. A current development concerns the use of FRET systems in homogenous fluorescent assays (sequence marking, fold boundary marking (proteins), DNS). In the process, the antigens and antibodies bought into reaction are marked with a fluorophore group, in which the one fluorophore functions as an energy donor and the other as a corresponding energy acceptor.

A comprehensive application of the FRET principle for the direct detection of molecule-molecule interactions in clinical laboratory diagnostics as well as in combinatorial pharmasynthesis requires the availability of these type of donors and acceptors, which are identified by efficient spectroscopic absorption and emission behavior in the long-wave spectral range, wherein the excitation wavelengths of the donor must be >350 nm in order to avoid an excitation of the biological substrate. Another essential criterion for their applicability in biological test methods is the formation of a stable, covalent biopolymer fluorophore compound without the stability and the biological activity of the marked molecule being negatively impacted in the process.

In view of the need for knowledge in this field, appropriate donor-acceptor systems are being sought, which meet the requirements for precision and short-term data availability, because known donor-acceptor systems have several disadvantages. Thus the transfer of energy from the donor to an acceptor is frequently not satisfactory and the sensitivity of the analytic method as a whole also suffers from this. Moreover, the complex stability of the donor frequently does not suffice and its water solubility is insufficient.

The causes of the described disadvantages lie to begin with in the composition, i.e., in the structure of the donor compounds. Creating compounds with high stability of the donor compound with the required spectroscopic properties of absorption and emission has not been successful so far. In addition, the acceptor dyes that have been used thus far are not the compounds of choice, because they are not coordinated in terms of their absorption maximum with respect to the emission spectrum of the donor and it has not been possible yet to guarantee sufficient solubility of the acceptor dye.

For a targeted application of the fluorophores, the priority development claim lies with the synthesis of new compounds in the increase of efficiency of the energy transfer from the donor to the corresponding acceptor and thus in an increase in the sensitivity of the analytical method. This claim can be taken into consideration by use of a lanthanide complex as an energy donor, in which a complexon with a special chromophorous group related to the application chelates the lanthanide(III)ion. The complex formation of the actual fluorophore, the lanthanide(III)ion, by a complexon should guarantee a high level of complex stability to the donor used and good solubility in an aqueous medium. The characteristic feature of these lanthanide(III) complexes used for the first time lies in the modification of the ligand system by substituents (designated as antenna in the following), which absorb in the planned wavelength range and can be coordinated with the excitation wavelength as a result.

The use of lanthanide(III) compounds and energy donors in fluorescence analysis should offer spectroscopic advantages as compared with organic donors with respect to sensitivity and signal-to-noise ratio and must therefore open up a multitude of application aspects, in particular also in combinatorial pharmasynthesis. The reason for this is the spectroscopic properties that are characteristic for the lanthanide(III) complexes, such as the large STOKES displacement, the line-like emission connected with high intensity as well as long lifetimes of the excited states. In addition, besides a time-resolved spectrogram, a decisive advantage of lanthanide(III) compounds lies in the favorable donor-acceptor distances, which make better signal separation and signal intensification possible vis-à-vis an incompletely marked substrate and permit a generally large label.

SUMMARY OF THE INVENTION

The objective of the invention is describing lanthanide(III) chelate complexes that are capable of energy transfers as donors, characterized by high stability as well as favorable spectroscopic properties of absorption and emission in the visible spectral range.

For the testing of lanthanide(III) complexes with respect to their donor properties a further objective lies in the selection and synthetic modification for the donor of spectroscopically suitable acceptor dyes and in the subsequent fluorescent examination of the donor-acceptor pair in a homogenous solution. Both new acceptor dyes as well as those that are known as such, e.g., rhodamine and polymethine dyes, are used as acceptor dyes, coordinated with the position of their absorption maximum with respect to the emission spectrum of the donor, their emission intensity and solubility in water.

The prerequisite for successfully marking the donor and acceptor is the presence of suitable groups with affinity on the respective fluorophore in order to make a covalent bond to the substrate molecule possible. As a result, a corresponding functionalization of the donor and the acceptor is required in the further course of things.

Then, a homogenous bioassay is supposed to be built, oriented with the functionalized donor-acceptor pair, upon a real and research-relevant biochemical formulation of a problem and the verification of the principle suitability of this donor-acceptor pair for the identification of biological molecule-molecule interactions is supposed to be furnished.

The objective consists therefore of creating a system in which an energy transfer from an antenna to a lanthanide(III) ion chelate forming agent is made possible. The practical application is given in that the group with affinity either to the antenna or to the chelate forming agent produces the link to biomolecules and can measure the energy transfer in this donor-acceptor system.

Then conclusions about the properties and the behavior of these molecules are possible. Possibilities for recording this type of measuring data include the FRET system among others.

Despite intensive worldwide research in this field and several promising approaches related to individual questions, there is no uniform theory, which explains the energy transfer from the antenna to the emitter and permits a working hypothesis to be put forward. It cannot be foreseen which antenna might be especially suitable. If one were to orient himself as an aid to the triplet state of the antenna chromophore, which lies energetically in a specific range and produces the corresponding antenna complex, he will be disappointed, because the triplet level changes dramatically with the complex formation of the rare earths. It is just as unforeseeable whether the chromophore 1,10-penathronline—substituted or unsubstituted—that we used is in a position to transfer the received energy to the SE (III) center.

DETAILED DESCRIPTION OF THE INVENTION

Figure 1:
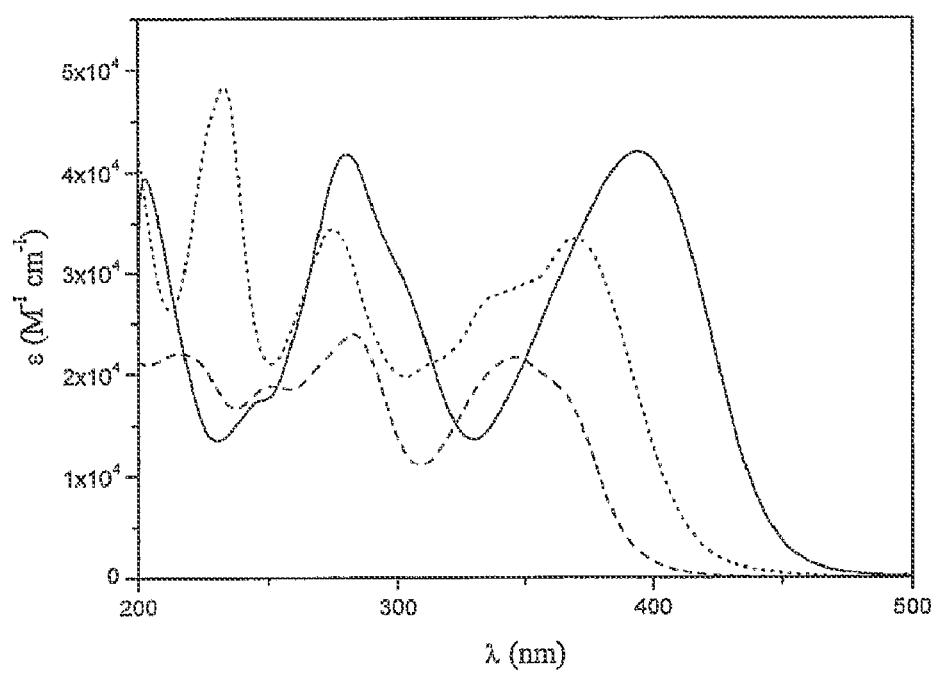
FIG. 1 shows the absorption spectra of the chromophores $PA_2$ (----), $PB_2$ (—) and P*B ($\cdots$) in MeOH.

The objective is attained in accordance with the invention in that antenna complexes of europium(III) and terbium(III) are produced in a first step. Antenna ligands are produced first for this purpose.

The framework of the sought after antenna ligand is comprised of the actual chelate ligand, which coordinates the metal ion and at the same time guarantees the high stability required for an application of lanthanide(III) compounds as donors. Secondly, the chelate ligand is supposed to have a chromophore group at its disposal, the antenna, which makes absorption of the donor in the visible spectral range possible.

Fluorescence lanthanide(III) compounds are already known, whose stability lies substantiated in their complex formation by O-functionalized ligand systems. According to the invention, a complexon, particularly diethylene triamine penta-acetic acid (LH$_5$), is selected for the sought after application aspect. In addition to the high complex stability, lanthanide chelates of complexons also show very good solubility in aqueous media. Because of the polydentate nature, a coordinative saturation of europium(III) or terbium(III) can be achieved despite the introduction of chromopohore group. In addition, additional functional groups can be introduced as groups with affinity, which make the fixation of a biological analyte possible.

The antenna that are composed of 4-ethinyl aniline and the chrompohore group determine, with their photo-physical properties, the excitation wavelengths and the efficiency of the energy transfer to the lanthanide(III)ion that is non-absorbing in the relevant spectral range both in the non-complexed form as well as the in the form complexed with LH$_5$. For an application of lanthanide(III) compounds as luminescence markers in biological systems, it is a special advantage that their excitation is possible in the visible spectral range, whereby direct excitation of biological substrates that are to some extent capable of fluorescence themselves can be excluded. As a result, according to the invention, these types of chromophores in, e.g., diethylene triamine penta-acetic acid, which absorb in the spectral range above 350 nm, are being introduced.

Conjugated 1,10-phenanthrolines substituted with acetylene groups represent chrompohores that are novel, efficient and fluorescent in the visible spectral range. The interest in these compounds has been based thus far exclusively on their application as fluorophores that can be modulated for building fluorescent sensors and switches in the field of molecular electronics. The absorption and emission wavelengths of these chromophores are determined by the type of substituents.

Because of their conjugated π system, 1,10-phenanthroline derivates are strongly absorbing chromophores and therefore suited in principle for the special application of the invention, wherein the absorption properties can be influenced with respect to the position of the absorption maximum and its intensity depending upon the substitution on the phenanthroline framework and functionality of the corresponding substituents. A primary amino function on the substituents is required in order to be able to introduce the desired chromophore into the chelate ligand. In addition to a symmetrical substitution of the 1,10-phenanthroline in the 3,8 position, one achieves another variation possibility of the spectroscopic properties of the chromophore above all with an asymmetrical substitution.

2-chloro-1,10-phenanthroline was described in accordance with the invention. The synthesis of the antenna chromophore P*B took place via a cross-coupling of 2-chloro-1,10-phenanthroline P* with ethinyl aniline (B).

P*B is a compound that is intensively absorbing into the visible spectral range. The absorption spectrum of P*B is depicted in FIG. 1 and the measured absorption values are summarized in Table 1. A comparison of the antenna chromophore P*B described for the first time with 1,10-phenanthroline (phen) shows that the substitution of the phenanthroline framework with the alkine B leads to a bathochrome displacement and intensification of the myriametric wave absorption (n→π* transition).

TABLE 1

Absorptions properties of the antenna chromophores $PA_2$, $PB_2$ and P*B as compared to 1,10-phenanthroline phen in MeOH.

| Antenna Chromophore | Absorption: $\lambda_{abs}$ in nm ($\epsilon$ in $M^{-1}$ $cm^{-1}$) |
|---|---|
| Phen | 230 (5.1 · $10^4$)/264 (3.0 · $10^4$)/280 (1.2 · $10^4$) |
| $PA_2$ | 216 (2.2 · $10^4$)/283 (2.4 · $10^4$)/348 (2.2 · $10^4$) |
| $PB_2$ | 280 (4.2 · $10^4$)/395 (4.2 · $10^4$) |
| P*B | 233 (3.8 · $10^4$)/275 (4.7 · $10^4$)/370 (3.4 · $10^4$) |

The coupling with B to P*B reinforces the shift to red of the absorption and intensifies it at the same time. In addition, the intensity ratios of the absorption bands to one another change.

In addition to stronger absorption, the antenna P*B at the same time shows a very intensive emission in the visible spectral range. The emission properties P*B, however, are not important in terms of the relevance for the future application of the antenna. The introduction of the antenna into the chelate ligand takes place via the transformation of the dianhydride LH-A of the diethylene triamine penta-acetic acid with the 1,10-phenanthroline derivate P*B with the formation of an amide bond. The relatively low reactivity of carboxylic acids as compared with primary amines requires an activation of the carbonyl components. In general, aminolysis of the corresponding acid chlorides, acid anhydrides or ester of the carboxylic acid is conducted as a result. In the case of the chelate ligand used, a complexon was first transferred to its dianhydride LH-A. The dianhydride LH-A is not just more reactive as compared to the free acid, but at the same time also increases product selectivity since only two of the five carboxyl groups are capable of a reaction with the aromatic amine. A reaction of the corresponding acid chloride or the ester would be unselective on the other hand.

Another advantage of this synthesis strategy with respect to the question posed by the invention consists of the fact that with the selection of the dianhydride not only the antenna, but also another amino-functionalized group can be coupled to the chelate ligand.

Synthesis of LH-A: Diethylene Triamine Penta-acetic Acid

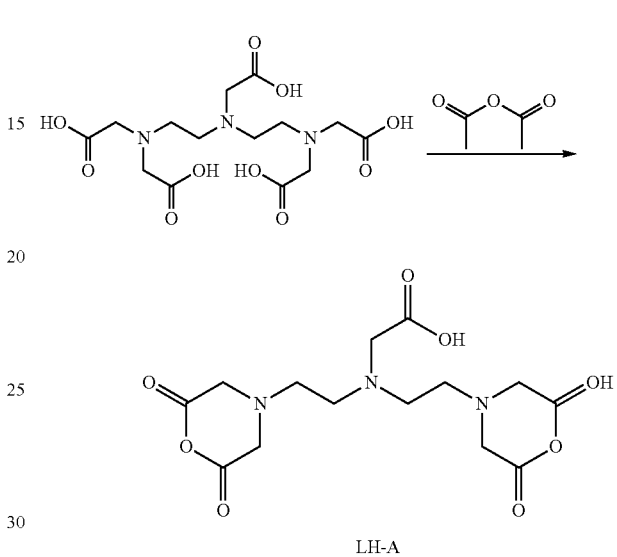

LH-A

The reaction is to be carried out using protective gas.

Add 13.4 g diethylene triamine penta-acetic acid to 12.9 mL acetic anhydride and 12.3 mL pyridine. Stir the suspension for 24 hours at 70° C. In the process, the reaction mixture will be stained dark brown. Filter after cooling and wash the product precipitate with acetic anhydride, then wash several times with hexane and dry in a vacuum.

Yield approx. 90%.

Synthesis of Antenna Ligand P*BLH$_4$

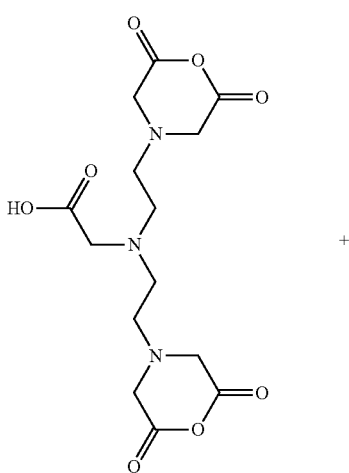

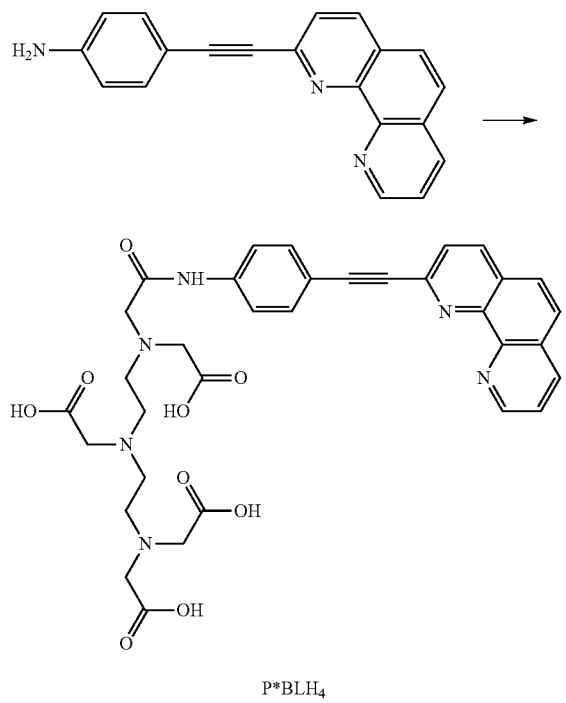

P*BLH$_4$

The reactions with dianhydride LH-A and the antenna P*B were conducted with a ratio of 1:1 with the goal of introducing only one antenna chromophore into the chelate ligand with the formation of P*BLH$_4$. Recovery took place in an aqueous solution, whereby the second anhydride function is opened.

Figure 2:
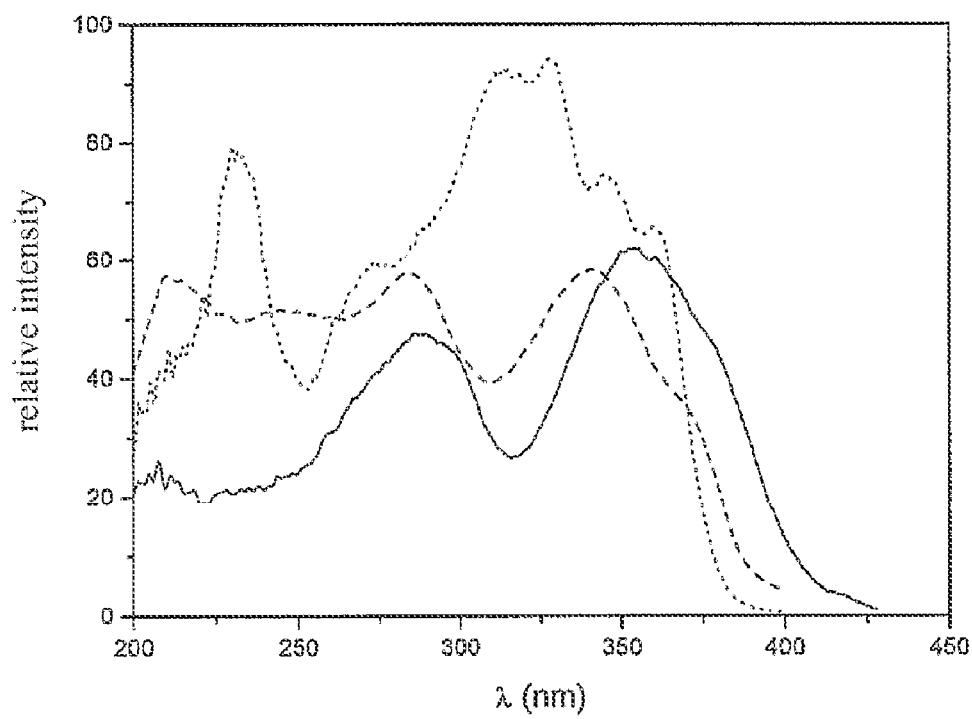
FIG. 2 shows the emission spectra of the antenna ligands $PA_2LH_4$ (----), $(PB_2)_2L_2H_6$ (—) and $P*BLH_4$ ($\cdots$) in $NH_3$/$H_2O$ with pH=10.

The introduction of the antenna P*B in the chelate ligand LH$_5$ itself does not produce any essential change in its spectroscopic properties, while the original chelate ligand, the diethylene triamine penta-acetic acid, now features all sought after spectroscopic properties of an antenna ligand. FIG. 2 illustrates the result obtained with the example of the excitation spectra recorded on a fluorescence spectrometer made by PERKINS ELMER (LS50B).

The absorption maximums of P*B are shifted slightly hysochromically by the linkage with diethylene triamine penta-acetic acid, whereby the intensity ratios of the absorption bands change and to some extent their band structure. In any case, however, the introduction of the antenna P*B in the diethylene triamine penta-acetic acid produces an intensification of the myriametric wave absorption as compared with the free antenna, while the spectral position of the emission is not affected.

Table 2 shows the spectroscopic properties of the antenna ligand P*BLH$_4$ in comparison with P*B. A particular advantage is that the excitation of the ligand does not have to take place in the absorption maximum of the antenna group since the position of the emission bands is independent of the excitation wavelength. At the same time, this makes possible any arbitrary long-wave excitation of the lanthanide(III) complexes in the range of their absorption, wherein the absorption range can be additionally expanded by the use of other chromophores.

TABLE 2

Absorption and emission maximums of the antenna ligand P*BLH$_4$ and the corresponding antenna chromophore P*B.

| Antenna Chromophore | | | Antenna Ligand | | |
|---|---|---|---|---|---|
| $\lambda_{abs}$ (nm) | ($\epsilon$ in M$^{-1}$ cm$^{-1}$) | $\lambda_{em}$ (nm) | $\lambda_{abs}$ (nm) | ($\epsilon$ in M$^{-1}$ cm$^{-1}$) | $\lambda_{em}$ (nm) |
| P*B  370 | 3.4 · 10$^4$ | 433 | P*BLH$_4$  311* | 3.5 · 10$^4$ | 433 |

*Excitation of P*BLH$_4$ takes place at $\lambda_{exc}$ = 360 nm.

The antenna ligand P*BLH$_4$ is used further to expand the attainment in accordance with the invention.

The stoichiometric transformation of the metal chlorides EuCl$_3$ and TbCl$_3$ with the antenna ligand P*BLH$_4$ as free acids in a weakly alkaline aqueous solution produces antenna complexes [EuP*BL]$^-$ and [TbP*BL]$^-$. The complexes can be precipitated after narrowing down the reaction solution by adding a suitable counterion (e.g., tetrabutyl ammonium ion "Bu$_4$N$^+$). For FRET examinations, however, only the metallic salt solutions were each titrated to the antenna ligand solution and the complex formation was controlled via US/Vis and fluorescence spectroscopy.

The antenna ligand with a group with affinity can also be described in principle in a so-called one-pot synthesis without isolation of the monoanhydride or the [P*BLH$_4$].

Synthesis of [EuP*BL]$^-$ and [TbP*BL]$^-$

The representation of the antenna complexes used takes place via titration of the metallic salt solutions to the antenna ligand solution:

EuCl$_3$ and TbCl$_3$ are added in a ratio of 1:1 to the BLH$_4$ (concentration>0.1 mM) in an aqueous solution with pH=6-7 or alkaline solution (NH$_3$/H$_2$O) with pH=10.

Figure 3:
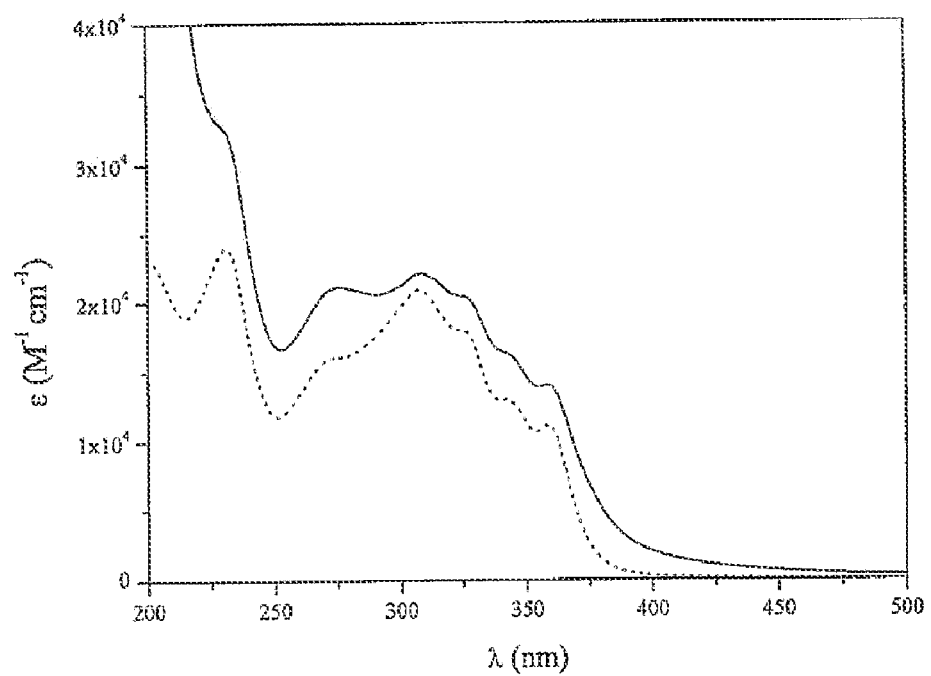
FIG. 3 shows the UV/Vis spectra of [EuP*BL]$^-$ (—) and [TbP*BL]$^-$ ($\cdots$) in $H_2O$.

Spectroscopic Characterization of Antenna Complexes [EuP*BL]$^-$ and [TbP*BL]$^-$ The absorption and emission spectra of antenna complexes [EuP*BL]$^-$ and [TbP*BL]$^-$ in an aqueous solution were recorded. The absorption spectra obtained from the two donors are depicted in FIG. 3.

Figure 4:
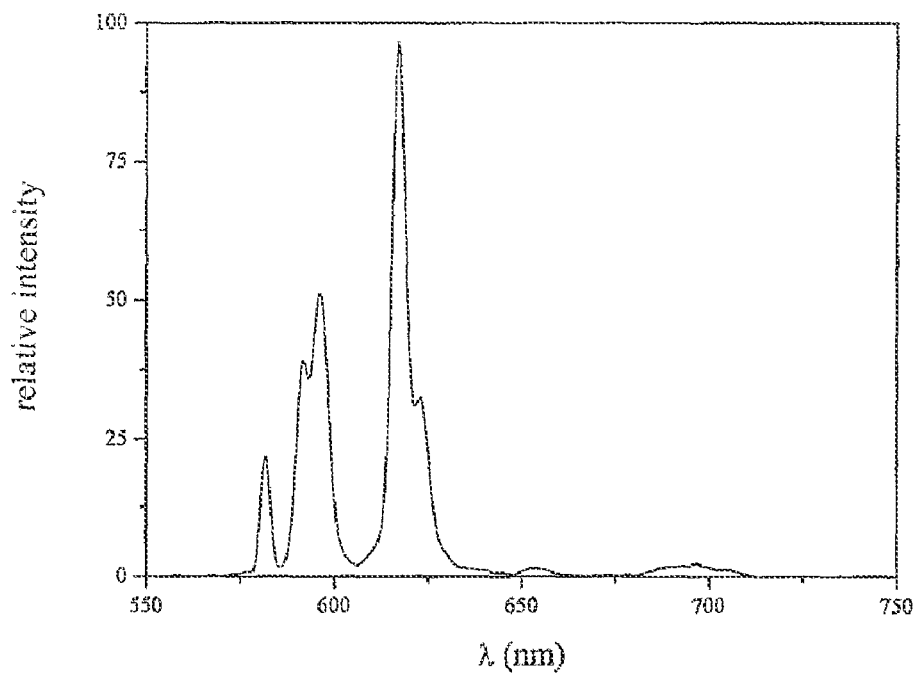
FIG. 4 shows the standardized emission spectrum of [EuP*BL]$^-$ in $H_2O$; (Emission conditions: $\lambda_{exc}$=360 nm, gap: 10/2.5 nm, dt=0.07 ms, gt=4.5 ms).

The light excitation of the antenna complexes [EuP*BL]$^-$ and [TbP*BL]$^-$ can now take place as desired in the absorption range of the antenna chromophore P*B. What is of interest in this case is an excitation that is as long-wave as possible, i.e., either in the absorption maximum of the n→π* transition from P*B or in the long-wave discharge of this absorption (as already mentioned with X$_{max}$=360 nm). As FIG. 4 shows, the red emission that is characteristic for the Eu(III)ion is the result for the antenna complex [EuP*BL]$^-$ from the excitation in the myriametric wave absorption of P*B.

Figure 5:
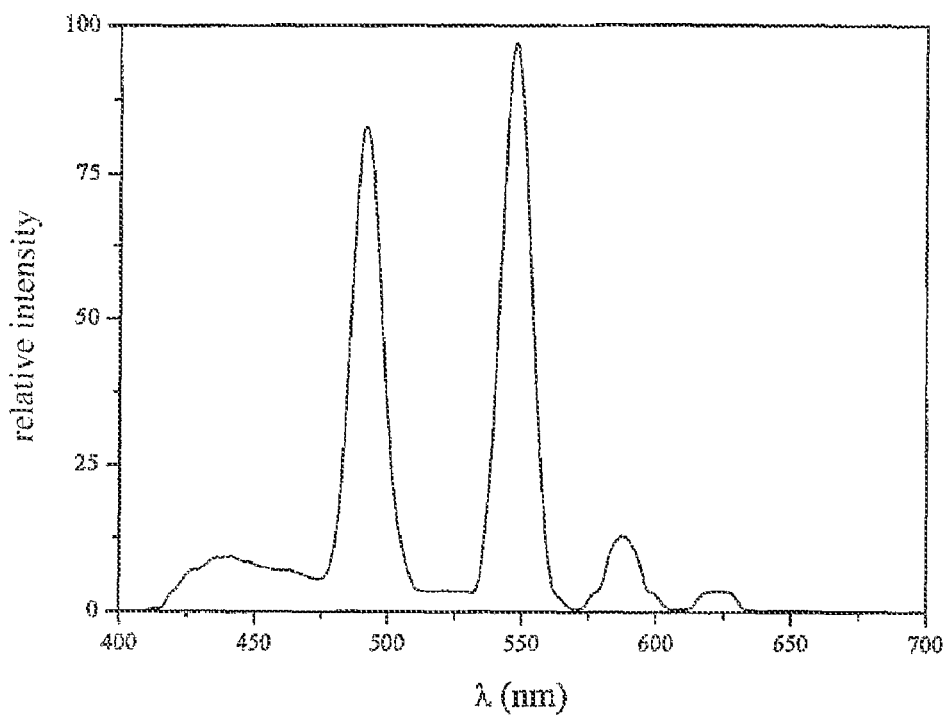
FIG. 5 shows the standardized emission spectrum of [TbP*BL]$^-$ in $H_2O$; (Emission conditions: $\lambda_{exc}$=360 nm, gap: 10/5 nm, dt=0.08 ms, gt=4.6 ms).

The sharp emission lines in the emission spectrum of [EuP*BL]$^-$ correspond to transitions within the 4f level. The most intensive transitions are observed at 595 nm and 617 nm. The emission of the terbium(III)ion, however, lies in the green spectral range, with the two most intensive emission lines at 492 nm and 547 nm. Analogous to [EuP*BL]$^-$, the emission spectrum of the antenna complex [TbP*BL]$^-$ that is depicted in FIG. 5 can be attributed to excitation of the antenna ligand in the myriametric wave absorption of P*B at $\lambda_{exc}$=360 nm.

The two lanthanide(III)ions show a very intensive emission in the antenna complexes [EuP*BL]$^-$ and [TbP*BL]$^-$. This intensive emission can be attributed to the strong absorption of the antenna chromophore P*B used. Compared with the emission spectra of the respective lanthanide(III) complexes of the unsubstituted diethylene triamine penta-acetic acid, the complex formation with the antenna ligand P*BLH$_4$ produces a 5-fold intensification of the metallic ion emission for [TbP*BL]$^-$ and a 30-fold intensification for [EuP*BL]$^-$, whereby the relative long life of the excited states is retained (Table 3).

TABLE 3

Lifetimes τ of the lanthanide (III) complexes in H$_2$O and the relative emission intensities of the chelates among one another in H$_2$O.

| Lanthanide (III) Complex | τH$_2$O (ms) | Relative Intensity |
|---|---|---|
| EuLH$_5$ | 0.62 | 0.03 |
| [EuP*BL]$^-$ | 0.59 | 1 |
| TbLH$_5$ | 1.90 | 0.2 |
| [TbP*BL]$^-$ | 1.61 | 1 |

One advantage of the described antenna complexes [EuP*BL]$^-$ and [TbP*BL]$^-$ lies in the comparatively long lifetimes of their electronically excited states. As Table 3 shows, a lifetime of the emission of 0.62 ms was observed for [EuP*BL]$^-$ and of 1.61 ms for [EuP*BL]$^-$, while lifetimes of organic fluorophores lie in the nanosecond range on the other hand.

With the use of lanthanide(III) compounds as donors, this now makes the recording of fluorescence spectra in a time-delayed measuring regime possible, i.e., recording the spectra does not take place directly after the excitation of the donor, but after a defined delay. All other arising and interfering background fluorescence of molecules with shorter lifetimes as compared with the donor (in our case antenna complexes [EuP*BL]$^-$ and [TbP*BL]$^-$) can thereby be eliminated and do not contribute to a falsification of the intensity of the actual measuring signal.

All fluorescence measurements of the donors [EuP*BL]$^-$ and [TbP*BL]$^-$ were tracked with a set time delay. The standard settings were as follows:

| For [EuP*BL]$^-$: | Excitation wavelength: $\lambda_{exc}$ = 360 nm |
|---|---|
| | Excitation gap: 15 nm   Emission gap: 5 nm |
| | Emission filter: 515 nm |
| | Time window (gt): 4.50 ms |
| | Time delay (dt): 0.07 ms |

| For [TbP*BL]$^-$: | Excitation wavelength: $\lambda_{exc}$ = 400 nm |
|---|---|
| | Excitation gap: 15 nm   Emission gap: 10 nm |
| | Emission filter: 430 nm |
| | Time window (gt): 4.60 ms |
| | Time delay (dt): 0.08 ms |

The same standard settings as for the FRET examinations were selected on the fluorescent spectrometer LS50B for the measurement of the fluorescence decay curves of the lanthanide(III) complexes. The emission was observed at a wavelength of $\lambda_{em}$=617.5 nm for [EuP*BL]$^-$ and $\lambda_{em}$=547 nm for [TbP*BL]$^-$.

In the following, the suitability of the donor complexes for attaining the objective in accordance with the invention is verified. To do this, the procedure described below will be used.

The FRET experiments examined the change in the lifetime and emission intensity of the electronically excited antenna complex [EuP*BL]$^-$ or [TbP*BL]$^-$ in the presence of various acceptor concentrations of ST936 or rhodamine B. The efficiency of the energy transfer is indicated by the extent of the quenching of fluorescence of the donor in the presence of an acceptor.

The donor-acceptor pairs are obtained by mixing corresponding donor and acceptor solutions. FRET examinations of the europium(III) complex [EuP*BL]$^-$ were conducted in accordance with the invention using the polymethine dye ST936 from SENSIENT GmbH in Wolfen as a corresponding acceptor. The rhodamine B dye was used as the acceptor dye for the antenna complex [TbP*BL]$^-$. In model systems, the selection of a donor and an acceptor is decided upon on the basis of their spectroscopic properties. Corresponding functionalizations on the donor or acceptor for a covalent bond linkage to a biological substrate are not of importance in this case.

Figure 6:
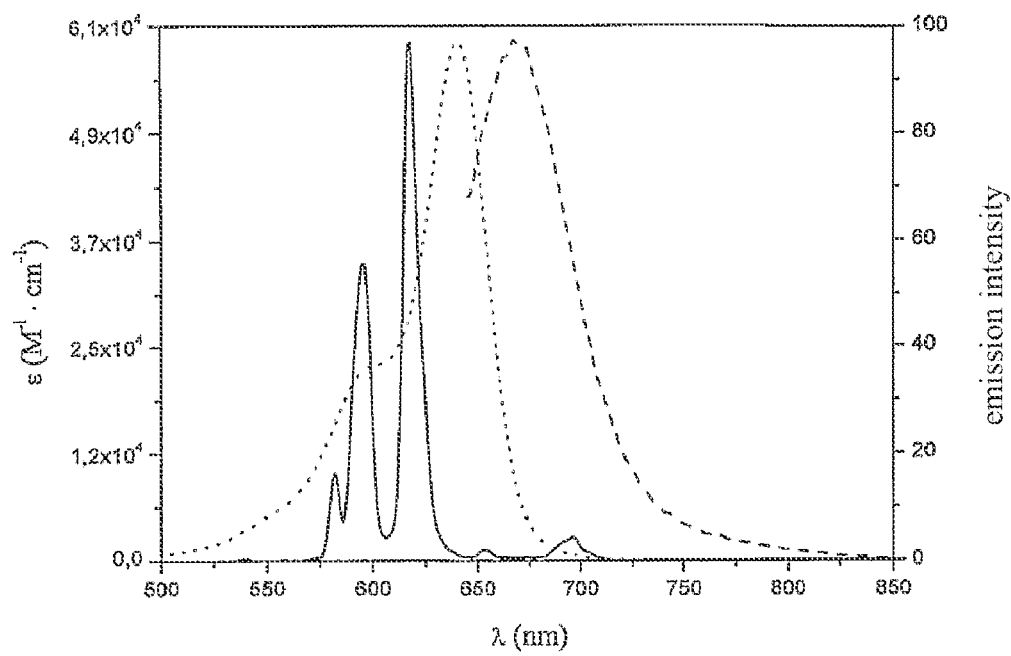
FIG. 6 shows the spectroscopic properties of [EuP*BL]$^-$ and ST936 in $NH_3$/$H_2O$ with pH=10 with absorption acceptors ($\cdots$) and donor emission (—) and acceptor emission (----).

The overlapping of the absorption of the acceptor with the emission of the donor is understood as the spectroscopic requirements of an acceptor for a selected donor in a FRET experiment. FIG. 6 shows the spectroscopic properties of the antenna complex [EuP*BL]$^-$ in relation to that of the selected polymethine dye ST936 from SENSIENT GmbH in Wolfen as a corresponding acceptor. It is evident that the emission spectrum of [EuP*BL]$^-$ and the absorption spectrum of the acceptor heavily overlap and thereby satisfy the requirement for the objective of the invention. In addition, the emission maximum of ST936 at $\lambda_{em}$=660 nm has a bathochrome displacement to the most intensive emission lines of the antenna complex.

The excitation of [EuP*B]$^-$ in the presence of polymethine dye ST936 produces a quenching of the emission intensity of the antenna complex and a build-up of the acceptor emission at 666 nm. A nonradiative energy transfer from the antenna complex [EuP*B]$^-$ used to the fluorescence dye ST936 is therewith verified. In the FRET experiment, a reduction of the emission intensity of [EuP*BL]$^-$ was observed with a constant donor concentration and a build-up of the emission of ST936 with an increasing acceptor concentration. With a required correction of the emission spectra, it is possible to determine the donor emission and sensitized acceptor emission for every donor-acceptor relationship.

If the antenna complex [TbP*BL]$^-$ and the acceptor dye rhodamine B selected for this donor are put in a solution, then the result for this donor-acceptor pair after excitation of [TbP*BL]$^-$ in the range of the myriametric wave absorption of the antenna chromophore P*B is also a quenching of the emission intensity of [TbP*BL]$^-$ due to the nonradiative energy transfer to the acceptor and a new emission of rhodamine B. Its suitability is therewith verified.

Acceptor dyes are synthesized after manufacture and the suitability test for the donors.

Polymethine dye ST936 from AcMaRi Chemie GmbH was found as a suitable acceptor for the donor complex [EuP*BL]$^-$ based on its spectroscopic properties in order to test the europium (III) complex for its energy donor properties in corresponding FRET experiments. This polymethine dye is characterized by strong absorption in the emission range of the donor and intensive emission with a bathochrome displacement to the emission of [EuP*BL]$^-$.

However, the poor solubility of the polymethine dye in aqueous solution and the lacking functionality for a covalent bond of the protein analyte being marked is disadvantageous for an application. As a result, the substitution of the polymethine dye ST936 by these types of groups that permit the possibility of binding, e.g., to proteins, and at the same time also improve solubility in water is required.

Within the framework of the invention, the goal consisted of derivatizing the indolenine group to build up new polymethine dyes suitable for marking while retaining the CY5 parent substance of ST936 and thus its absorption and emission properties with respect to the position of the maximums.

Starting with the indolenine derivatives TIPBr⁻, TIEOBr⁻, TIPEBr⁻, TIPNBr⁻ and TIBEI⁻, additional dyes were described in addition to the already known polymethine dye course of things the second anhydride function can also be transformed with an amino-functionalized group.

In this case two different linker groups, diamines with different chain lengths, were bound to the antenna ligand P*BLH$_4$. P*BLH$_3$-EDA (EDA: ethylene diamine) and P*BLH$_3$-SP1 (SP1: 1,8-diamino-3,6-dioxaoctan) were synthesized.

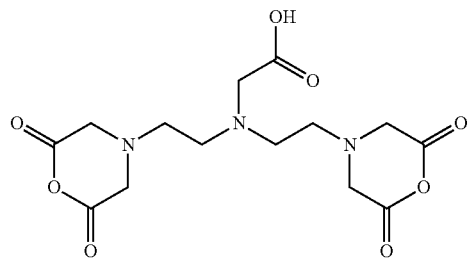

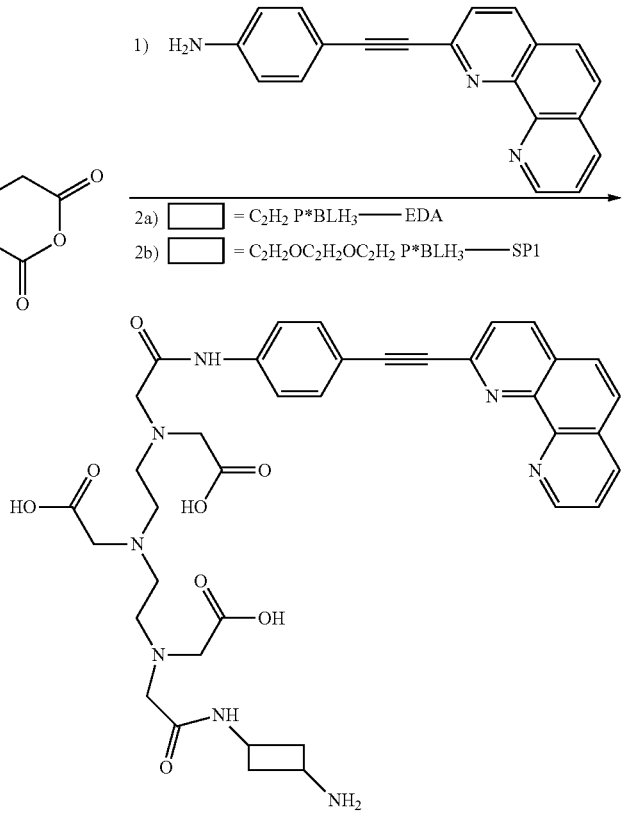

ST936: Cy5BE, Cy5'BE and Cy5PE. Cy5EE was obtained as a corresponding polymethine dye from the transformation of the indolenine derivative TIEOBr⁻ with dianilide. In the process, the hydroxy function was esterified by the acetic anhydride found in the reaction solution.

It was recognized that the antenna ligand must possess a functionality that permits a covalent bond of the analyte being determined (the immunoassay component) to the subsequent donor. The bond of the analyte via this functional group reduces the number of free carboxylate groups on the antenna ligand, which groups complex the lanthanide(III)ion and therewith change the total charge of the antenna complex that is forming. For FIA systems based on FRET, only negatively charged or neutral complexes are advantageous since they cannot enter into any non-specific bonds with the biological, for the most part also negatively charged, substrate. To begin with, the lanthanide(III) antenna complexes [LnPB]⁻ were manufactured for spectroscopic characterization.

In addition, the antenna ligand P*BLH$_4$ is functionalized in accordance with the invention by the introduction of linker groups. This is possible because it became known that the dianhydride of the diethylene triamine penta-acetic acid LH-A only reacts unilaterally with the 1,10-phenanthroline derivate P*B substituted in the 2 position so that in the further The reaction is to be carried out using protective gas.

Dissolve 1.5 mmol LH-A in 24 mL DMF and 2.1 mL Et3N, and mix dropwise while stirring with 1.5 mmol 2-(4-aminophenyl ethinyl)-1,10-phenantholine (P*B), dissolved in 5 mL DMF. After stirring for approx. 2 hours at room temperature, add drops of the reaction solution to 2 mmol diamine in 3 mL DMF, whereby a yellow flaky precipitate forms. Stir for another 1-2 hours, evaporate somewhat in a vacuum and place overnight in the refrigerator, wherein the product should precipitate completely. Separate the product precipitate from the reaction solution via a glass frit, wash with somewhat dry methanol and ether and then dry in a vacuum. The product will be preserved as a yellow solid. If one isolates the product in the air, the yellow precipitate becomes viscous and turns an orange red color. The product can be dried in the air and pulverized with a mortar.

Yield approx. 60%.

The polymethine dyes were also functionalized because an objective of the invention was for one to describe a polymethine dye with a free carboxyl group, via which the dye can be directly bound to a protein, whereby the carboxylic acid group also permits derivatization with groups having other reactivity (e.g., diamines). On the other hand, a polymethine dye was supposed to be synthesized whose chemical coupling to a protein analyte does not take place via the formation of an amide bond.

For this reason, the two symmetrical dyes Cy5BE and Cy5PE as well as the asymmetrical Cy5'BE were described for the first aspect. The desired carboxylic acid function was then obtained directly from the hydrolysis of the ester dye and the dye could be isolated as perchlorate.

FRET experiments with a defined donor-acceptor distance were conducted with the goal of modeling a bioassay.

In the model system, the spacer brings the donor and acceptor in a spatial distance and simulates the binding interactions of biomolecules (e.g., antigens and antibodies), linker-linker.

In the process, the chain length of the linker of the donor-acceptor distance may not get so large that FRET can no longer be observed, i.e., it must range within the so-called Forster distance.

Figure 11:
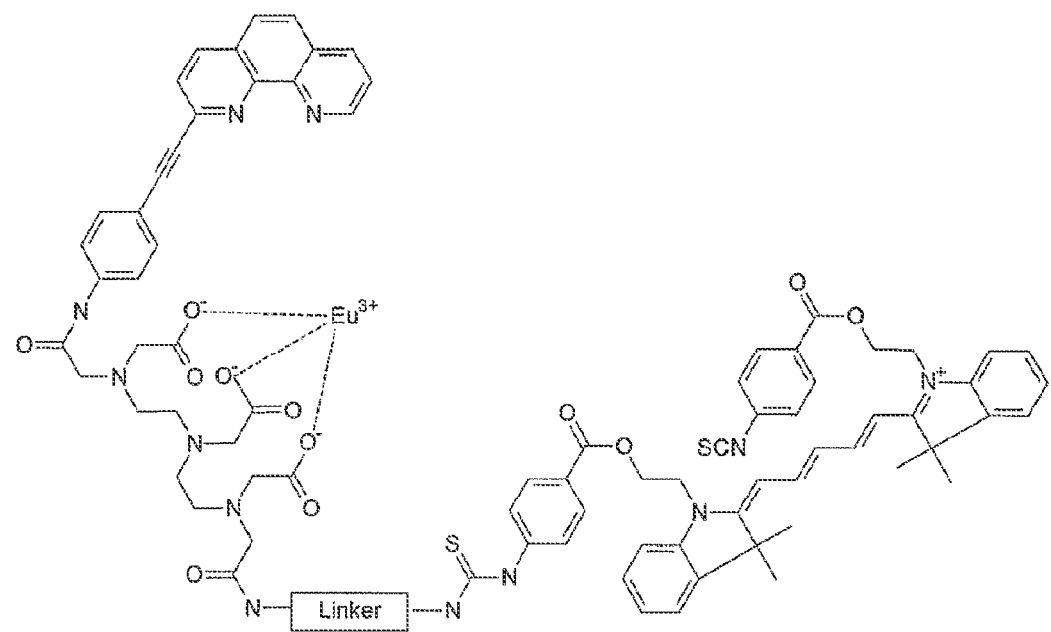
FIG. 11 shows the chemical structure of a model system with a modified donor and acceptor.

In this model system, the donor and acceptor are firmly linked via the isothiocyanate function of the modified dye with a variation of the chain length of the linker in the form of an amide (donor-linker bond) or a thiocarbamate bond. The sought after model system with a modified donor and acceptor is reproduced in FIG. 11. The antenna complex [EuP*BL]$^-$ was used as the donor with the substitution of the antenna ligand with the diamines ethylene diamine (EDA) or 1,8-diamino-3,6-dioxaoetan (SP1). The corresponding acceptor in the FRET experiment was the polymethine dye Cy5ENCS.

Donor (antenna complex [EuP*BL]$^-$) and acceptor (polymethine dye Cy5ENCS) are bound with one another via a linker. Ethylene diamine (EDA) or 1,8-diamino-3,6-dioxaoctan (SP1) were used as the linker.

The donor was prepared via titration of an aqueous EuCl3 solution ($\geq 1.10-3$ M) to an equimolar aqueous solution of antenna ligand P*BLH3-EDA or P*BLH3-SP1. The formation of the antenna complex [EuP*BL-EDA] and/or [EuP*BL-SP1] was tracked using fluorescence spectroscopy. After excitation of the aqueous solution at $\lambda_{EXC}=360$ nm, complex formation of [EuP*BL-EDA] and/or [EuP*BL-SP1] was confirmed with the observation of the intensive red emission of the europium(III)ion.

Figure 7:
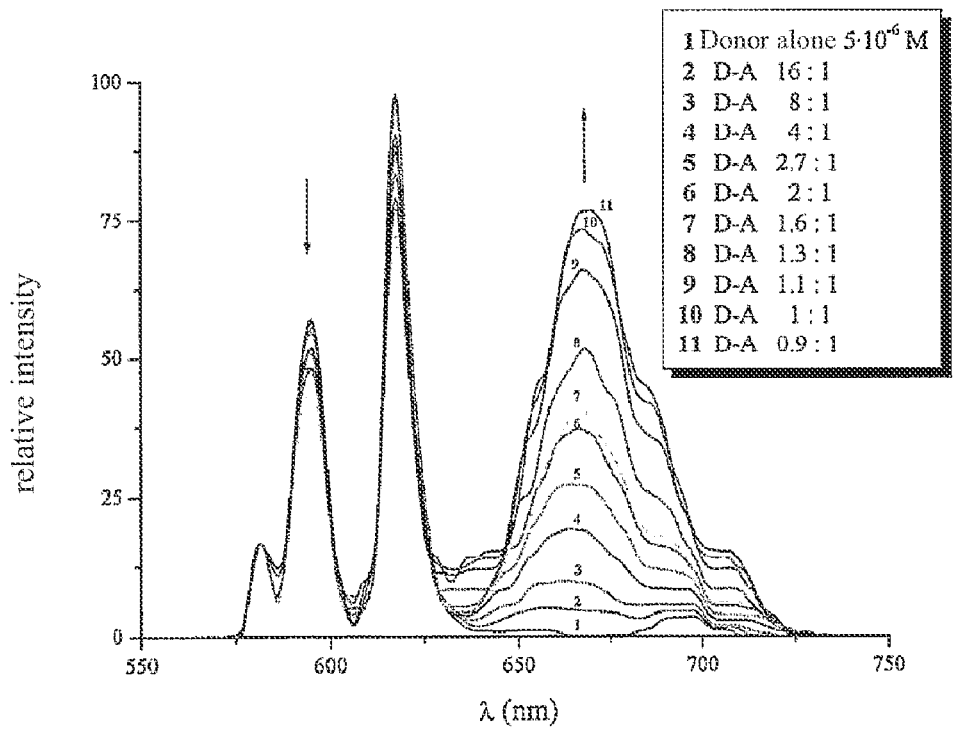
FIG. 7 shows a FRET experiment of [EuP*BLH$_3$]-EDACy5ENCS in $H_2O$; corrected emission spectra as a function of increasing acceptor concentration ($C_{DONOR}$=5*10$^{-6}$ M, $C_{ACCEPTOR}$=1.6*10$^{-7}$ M to 5.6*10$^{-6}$ M).

In a FRET experiment to dissolve the antenna complex [EuP*BL-EDA] and/or [EuP*BL-SP1] that was substituted with terminal amino function, a constant concentration of the acceptor dye Cy5ENCS was added step-by-step until there was an excess of polymethine dye. In the process, the emission of the donor [EuP*BL-EDA] (the same applies to the [EuP*BL-SP1]) is quenched with an increasing acceptor concentration and a build-up of the emission of the acceptors is observed. FIG. 7 graphically depicts the emission spectra obtained from the FRET experiment, after correction, for the donor-acceptor pair {[EuP*BL]-EDA-Cy5ENCS}. The correction corresponds to a standardization of all emission spectra to the maximum of the most energy-rich transition of the antenna complex with the presence of the acceptor.

Under the same measuring conditions, the FRET experiments of the modified antenna complex were conducted in the presence of the linker SP1 with {[EuP*BLH4]-SP1-Cy5ENCS}. A quenching of the donor emission with simultaneous sensitization of the emission of the polymethine dye is also observed in this case.

As a result, the applicability in principal of the new FRET systems for corresponding immunoassays is herewith verified.

FRET Bioassay with Modified Donor-acceptor Pair

The measuring system that uses one of the described donor-acceptor pairs is supposed to be as universally useable as possible for verifying and/or quantifying biologically active molecules with a FRET bioassay. As a result, experiments were performed to see whether binding protein A to immunoglobulin (IgG) after marking both partners with the antenna ligand P*BLH3-SP1 as donor and the dye Cy5BA as acceptor could be verified using a FRET measurement.

The advantage of the protein A-IgG system used is that binding protein A to the IgG occurs on the Fc fragment, whereby the interaction of the IgG with the corresponding antigen, which binds to the Fab fragment, is not affected.

For the ligandization of the two proteins used with the donor and/or the acceptor, the two reactants were treated in the weakly acidic range with an excess of N-ethyl-N'-(3-dimethylaminopropyl)-carbodiimide (EDC) at 20° C. and the acid amides of the antenna ligand and/or of the dye that form were separated with the protein by gel filtration from the unconverted ligand and other low-molecular components of the reaction preparation.

Coupling of P*BLH$_3$-SP1 to IgG 0.066 µMol IgG was mixed with 3.3 µMol of the antenna ligand P*BLH$_3$-SP1 and 330 µMol EDC in 100 mM imidazole/HCl buffer, pH 5.0, and incubated at room temperature overnight. After 1 hour of incubation the pH value was again brought to pH 4.5-5.0 with 1 N NaOH. On the next morning, precipitated material, which essentially represents denatured protein, was removed by centrifugation at 5000×g and the IgG antenna ligand conjugate was separated by gel filtration via a NAP 5 column (Amersham Biotech) from unconverted antenna ligand and other low-molecular substances.

The yield was approx. 60% related to the IgG that was used. An IgG molecule contains approximately 30 bound molecules of the antenna ligand. This degree of substitution can be set as desired by varying the molar protein-antenna ligand ratio.

The synthesis of the adduct from protein A and the dye Cy5BA took place in an analogous manner, however, the dye was used as an alcoholic solution because of its poor water solubility. Recovery took place as described above by separating the precipitated protein via centrifugation and separation of the unconverted dye via gel chromatography.

The yield was approx. 10% (related to Protein A), the degree of substitution was at approx. 8 Mol dye per Mol of protein A. The poor yield is caused by a strong denaturation of the protein by the alcohol used as the solvent for the dye.

The qualification of the bond donors and acceptors for FRET was tested on the basis of lifetime experiments with two different concentrations of the marked components protein A (PA) and immunoglobulin G (IgG) in a ratio of PA:IgG of 1:1. The energy transfer efficiency E determined from the lifetime measurements in this case must be independent of the concentration of the components. Solutions were manufactured from the obtained marked material in imidazole/HCl buffer of $8.5*10^{-7}$ and $2.5*10^{-7}$. The donor complex was manufactured by adding the quantity of EuCl$_3$ solution corresponding to the marker portion to the ligand.

Figure 8:
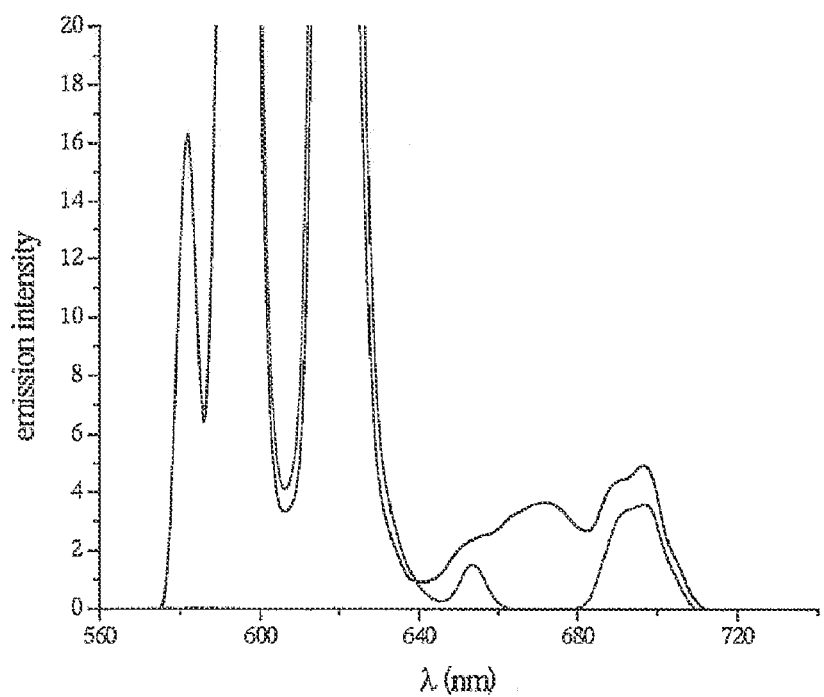
FIG. 8 shows the fluorescence spectra with C(IgG)=C (PA)= 2.5*10$^{-7}$ M (dotted line=IgG, solid line=IgG+PA).
Figure 9:
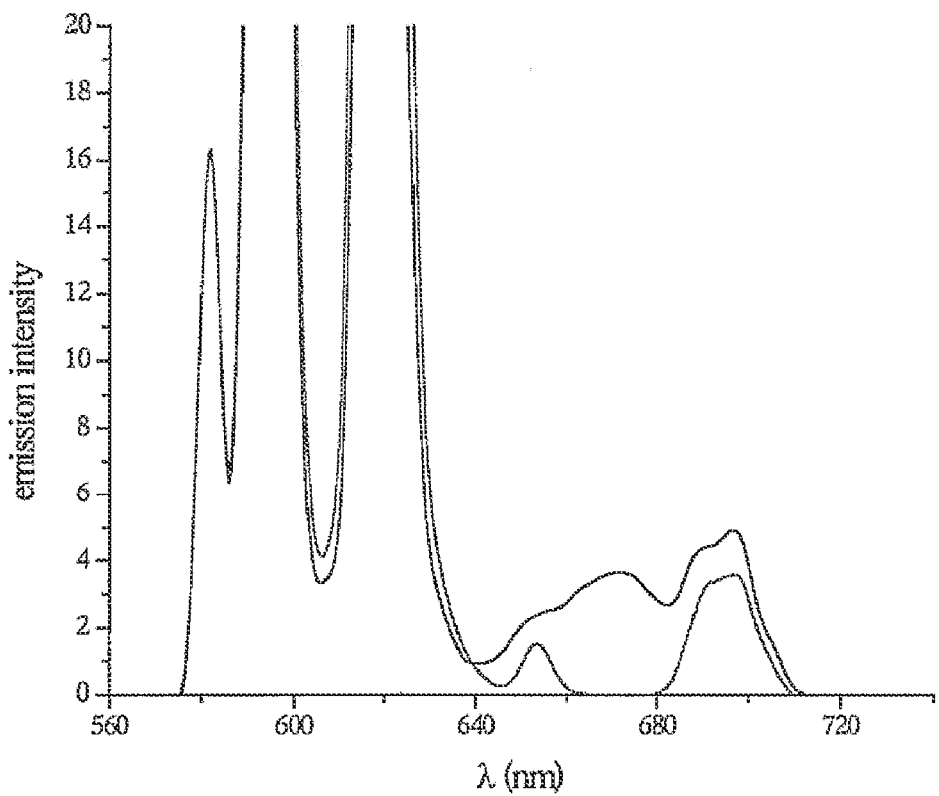
FIG. 9 shows the fluorescence spectra with C(IgG)=C (PA)= 8.2*10$^{-7}$ M (dotted line=IgG, solid line=IgG+PA).

FIGS. 8 and 9 show the spectra obtained with the indicated concentrations under the corresponding excitation conditions. The pure donor solution was always tested first and $\tau_0$ was determined and the tests were repeated after the addition of the marked protein A in order to determine $\tau$. The lifetime was measured four times and the mean value was used. The transfer efficiency in % is yielded from:

$$E = 1 - \frac{\tau}{\tau_0}$$

The measured values are summarized in Table 4. The transfer efficiency is consequently independent in the course of the method-contingent measuring error and the serviceability of the system at hand is proven. The relatively small amount of the efficiency has its cause in the comparison to the acceptor with a higher degree of marking of the donor (30:8). In this case, a ratio of 1:1 or 1:2 (IgG:PA) would be more favorable.

TABLE 4

| Concentration in M | | Measured Lifetime | | | | Mean Value τ | E in % |
|---|---|---|---|---|---|---|---|
| 8.2*10⁻⁷ | IgG | 0.4780 | 0.4784 | 0.4758 | 0.4774 | 0.4774 | 19 |
|  | IgG + PA | 0.3865 | 0.3876 | 0.3870 | 0.3863 | 0.3869 |  |
| 2.5*10⁻⁷ | IgG | 0.5177 | 0.5154 | 0.5170 | 0.5040 | 0.5135 | 17.3 |
|  | IgG + PA | 0.4184 | 0.4367 | 0.4050 | 0.4395 | 0.4279 |  |

Proposal for Putting Together a Building-Block System for a FRET Immunoassay

Building-block systems are supposed to be developed for the use of the FRET immunoassay in biological and/or medical analytical practice, which provide the user with the simplest possible handling of the analysis system and a high degree of flexibility with respect to the primary antibody used and therefore the selection of analytes being tested.

Figure 10:
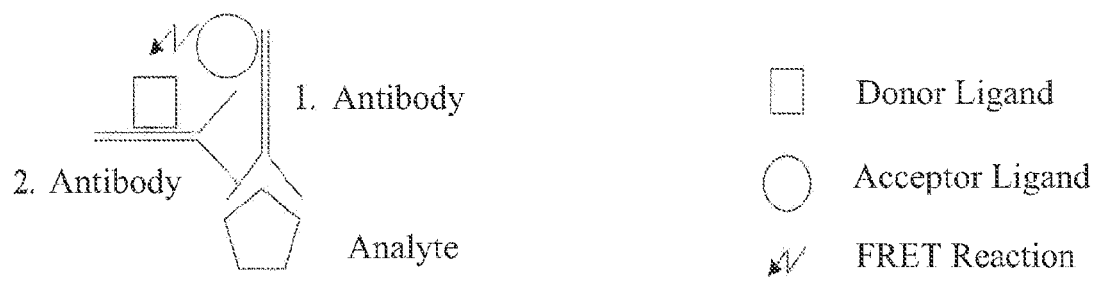
FIG. 10 shows a schematic depiction of the measuring principle of a FRET immunoassay.

FIG. 10 schematically depicts the measuring principle of a FRET immunoassay. In a first reaction, the test material with the analyte is incubated with an antibody (primary antibody), which is coupled to the donor. A second reaction step verifies the bound primary antibody with a second antibody marked with the acceptor dye or another protein (e.g., protein A or protein G), which specifically binds immunoglobulins. The FRET reaction triggered by this protein-protein interaction is then the measurable variable of the assay. This type of FRET immunoassay must take place like a solid phase like a classic ELISA reaction since otherwise there is a risk that the secondary antibody will produce a FRET reaction with unconverted primary antibodies.

Schematic Representation of a FRET Immunoassay

A kit for a FRET immunoassay is comprised of the antenna ligand and the reagents (EDC, buffer, gel filtration column) for its coupling to the primary antibody to be provided by the user as well as the secondary antibody marked with the acceptor dye (or another protein, which specifically binds immunoglobulins). If several secondary antibodies are enclosed with the kit, which are marked with acceptor dyes and which differ in terms of their spectral properties so that the detection of the FRET reaction can be conducted using different wavelengths, simultaneously detecting different analytes (multiplexing) is possible with such a measuring system.

In the case of the donor, a system consisting of the amino-functionalized antenna P*B, the acid hydride LH-A and the spacer ethylene diamine EDA have proven to be effective. The three components are linked to the antenna ligand in DMF/TEA. A variation of the spacer is possible in principle. The products obtained are also useable after chromatographic cleaning and are made available to the user as solids. Antibody and antenna ligand are linked to one another [with A (sic)] according to the normal method with the activation of the carbonyl component with N-ethyl-N'-(3-diamethyl aminopropyl)-carbodiimide (EDC) or N,N'-carbonyl diimide azole (CDI) via the formation of amide bond. In order to expand the range of application, transformation to an isothiocyanato function on the terminal amide nitrogen with the antenna ligand that is provided with a spacer is also possible.

The actual energy donors, the lanthanide(III) complexes, are represented in the assay in situ by adding the corresponding quantity of a solution of metal chloride. The selection of the lanthanide(III)ion determines through its specific emission the selection of the acceptor dye. For the europium(III) ion that is used as an example, the polymethine dyes Cy5R were selected, whose absorption lies in the emission range of the donor (europium(III) complex). Hydroxy dyes and Cy5 dyes functionalized with acid groups are accessible in high yields. The acidic function permits a direct link to the secondary antibody via an amide bond in accordance with the method already cited in the case of the donor. The hydroxy-functionalized dye can also be linked with the carboxyl groups of a protein via an ester bond. Compounds from the class of polymethine dyes are indicated as functional example as well as polymethine-like dyes, which are manufactured and used in accordance with the invention.

In the simplest case, the commercial building-block system in accordance with the invention consequently contains at minimum of the following components (Table 5):

The antenna ligand with the spacer EDA as a solid (component 1).

CDI or EDC and triethylamine acetate buffer for marking. Europium(III)chloride as $10^{-3}$ mol/l solution in water (component 2).

The secondary antibody marked with a Cy5 dye (component 3)

| Component 1 | Component 2 | Component 3 | Excitation Wavelength $\lambda_{exc}$ [nm] | Detection Wavelength $\lambda_{exc}$ [nm] |
|---|---|---|---|---|
| P*BLH-EDA | Eu³⁺ | Cy5BA | 360 | 665 |
| P*BLH-EDA | Tb³⁺ | Cy3BA | 360 | 550 |

The FRET immunoassay described above is preferably performed on a solid surface (e.g., microtiter plate or glass slide in the case of histochemical applications) so that primary antibodies that are not bound to the analytes, which would supply false positive signals in the subsequent FRET reaction, can be removed by a washing step before the FRET reaction.

A homogenous FRET immunoassay is also conceivable for some applications. An example of this is the screening of hybridoma cell clones for antibody production. In addition to the primary antibody, which recognizes the monoclonal antibodies (e.g., anti-mouse IgG) this type of system contains a protein as a second component such as the complement factor C1q so that it is possible to differentiate antigen-antibody complexes from free immunoglobulins.

The main problem with homogenous applications is the possibility of obtaining an incorrect result because the distance between the donor and acceptor is so great that no FRET can be observed despite the presence of a protein-protein interaction. This risk of misinterpretation can be circumvented if the experiment is conducted in the form of a normal competitive assay. In this case, it is necessary to start with an AK/AG pair with a very weak interaction in which FRET is verifiable. After adding an unmarked antibody, the formation of a more effective complex can be detected from the reduction of the emission intensity of the acceptor as a function of the concentration of this antibody.

Catalog of Synthetic Substances 3,8-dibromophenanthroline (P)

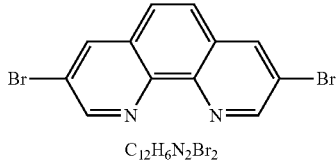

$C_{12}H_6N_2Br_2$ mp: 276° C.
$^1$H-NMR (ppm, CDCL$_3$):
9.18 (d, 2H phen-2,9), 8.41 (d, 2H phen-4,7), 7.76 (s, 2H phen-5.6)
IR (cm$^{-1}$, KBr):
3025 m, 1617 m, 1586 s, 1574 m, 1478 m, 1414 s, 1372 m, 1208 s, 1103 s, 1035 m, 906
s, 894 s, 784 s, 722 s, 509 w
EI-MS (m/z M$^+$): 337.9 Calculated: 338.00.

1-methyl-1,10-phenanthroline-1-iumiodide (P*(a))

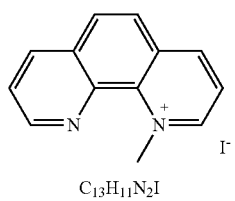

$C_{13}H_{11}N_2I$ mp: 210-213° C.
$^1$H-NMR (ppm, D$_2$O):
9.07 (s, 1H phen-9), 8.89 (d, 2H phen-4,7), 8.12 (d, 2H phen-3,8), 7.75 (s, 2H phen-5,6),
7.63 (s, 1H phen-2), 4.98 (s, 3H CH$_3$)

1-methyl-1,10-phenanthrol-2-on (P*(b))

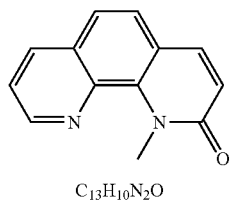

$C_{13}H_{10}N_2O$ mp: 123-124° C.
$^1$H-NMR (ppm, CDCl$_3$):
8.88 (d, 1H phen-9), 8.12 (d, 1H phen-7), 7.73 (d, 1H, phen-4), 7.50 (s, 2H phen-5,6), 7.45 (m, 1H phen-8), 6.92 (d, 1H phen-3), 4.43 (s, 3H CH$_3$)

2-chlorophenanthroline (P*)

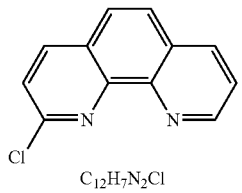

$C_{12}H_7N_2Cl$ mp: 129-130° C.
$^1$H-NMR (ppm, MeOH-d$_4$):
9.01 (d, 1H phen-9), 8.37 (m, 2H phen-4,7), 7.86 (d, 2H phen-5.6), 7.71 (m, 2H phen-3,8)
EI-MS (m/z M$^+$): 214.0 Calculated: 214.03.

3-(2-hydroxy-2-methylbut-3-inyl)aniline (A(a2))

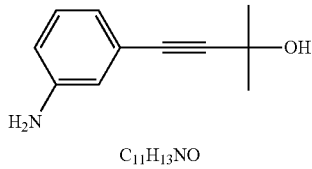

$C_{11}H_{13}NO$ mp: 114-115° C.
$^1$H-NMR (ppm, CDCl$_3$):
7.08 (t, 1H Ph), 6.82 (d, 1H Ph), 6.74 (s, 1H Ph), 6.63 (dd, 1H Ph), 3.03 (br s, 2H NH$_2$),
1.60 (s, 6H CH$_3$), 1.25 (s, 1H OH)
$^{13}$C-NMR (ppm, CDCl$_3$):
146.9 (C—NH$_2$), 129.9 (Ph), 124.1 (Ph), 122.8 (Ph), 118.6 (Ph), 115.9 (Ph), 93.9 (C≡C),
83.0 (C≡C), 66.3 (C(CH$_3$)$_2$), 32.2 (CH$_3$)
IR (cm$^{-1}$, KBr):
3382 s, 3204 s, 2980 s, 2932 m, 2220 w, 1600 s, 1582 s, 1485 s, 1446 s, 1372 m, 1360 m, 1295 m, 1228 s, 1160 s, 1131 s, 973 m, 943 s, 891 s, 872 s, 794 s, 691 s, 662 m, 571
w, 553 w, 534 w, 481 m, 464 w
EI-MS (m/z M$^+$): 175.1 Calculated: 175.301.

3-ethinyl aniline (A)

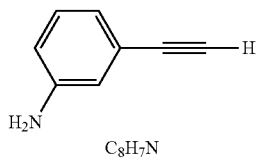

$C_8H_7N$ bp: 68° C. with p=3.9·10$^{-1}$ Torr
$^1$H-NMR (ppm, C$_6$D$_6$):
6.97 (d, 1H Ph), 6.83 (t, 1H Ph), 6.58 (s, 1H Ph), 6.15 (dd, 1H Ph), 2.73 (s, 1H≡CH), 2.68
(br s, 2H NH$_2$)
$^{13}$C-NMR (ppm, C$_6$D$_6$):
147.7 (C—NH$_2$), 130.1 (Ph), 124.1 (Ph), 122.9 (Ph), 118.9 (Ph), 116.2 (Ph), 85.2 (C≡C),
77.8 (C≡C)
IR (cm$^{-1}$, KBr):
3443 s, 3362 s, 3287 s, 3047 m, 2107 m, 1622 s, 1530 m, 1488 s, 1446 s, 1316 s, 1285 s, 1156 s, 995 s, 932 s, 867 s, 788 s, 689 s, 533 s, 460 s

4-(2-hydroxy-2-methylbut-3-inyl)aniline (B(a2))

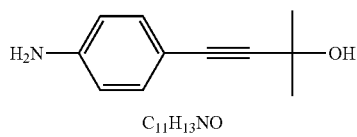

mp: 79° C.
$^1$H-NMR (ppm, CDCl$_3$):
7.22 (d, 2H Ph), 6.59 (d, 2H Ph), 3.77 (s, 2H NH$_2$), 1.59 (s, 6H CH$_3$)
$^{13}$C-NMR (ppm, CDCl$_3$):
147.2 (C—NH$_2$), 133.7 (Ph), 115.3 (Ph), 112.8 (Ph), 92.2 (C≡C), 83.3 (C≡C), 66.4 (C(CH$_3$)$_2$), 32.2 (CH$_3$)

4-nitrophenylacetylene (B(b3))

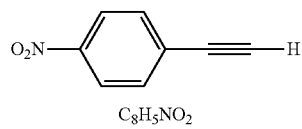

mp: 150° C.
$^1$H-NMR (ppm, MeOH-d$_4$):
8.23 (d, 1H Ph), 7.69 (d, 1H Ph), 3.93 (s, 1H≡CH)

4-ethinyl aniline (A)

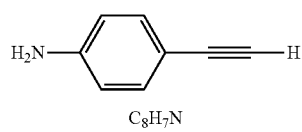

mp: 99-100° C.
$^1$H-NMR (ppm, C$_6$D$_6$):
7.32 (d, 2H Ph), 6.03 (d, 2H Ph), 2.76 (s, 1H≡CH), 2.71 (br s, 2H NH$_2$)
IR (cm$^{-1}$, KBr):
3486 s, 3388 s, 3305 w, 3260 s, 3036 w, 2098 s, 1618 s, 1512 s, 1305 s, 1178 s, 829 s, 672 m, 605 m, 532 s

3,8-bis(3'-aminophenylethinyl)-1,10-phenanthroline (PA$_2$)

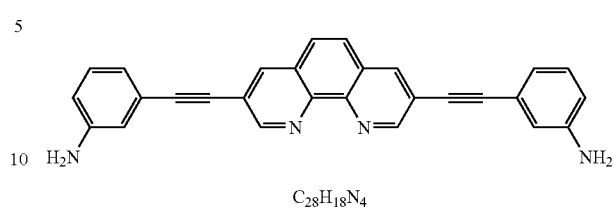

mp: 252° C.
$^1$H-NMR (ppm, CDCl$_3$):
9.18 (d, 12 phen-2,9), 8.71 (d, 2H phen-4,7), 8.05 (s, 2H phen-5,6), 7.11 (t, 2H Ph), 6.84 (s, 2H Ph), 6.79 (d, 2H Ph), 6.67 (d, 2H Ph)
$^{13}$C-NMR (ppm, DMSO-d$_6$):
151.5 (phen-C2,9), 148.9 (C—NH$_2$), 140.0 (phen-C4,7), 138.2 (Ph), 129.4 (phen-C5,6), 127.2 (Ph), 121.7 (phen-C3,8), 118.9 (Ph), 116.2 (Ph), 115.2 (Ph), 94.7 (C≡C), 85.2 (C≡C)
EI-MS (m/z M$^+$): 410.0 Calculated: 410.153.
UV/Vis spectra (MeOH):
$\lambda_{abs}$=($\epsilon$ in M$^{-1}$ cm$^{-1}$): 216 (2.2·10$^4$); 283 (2.4·10$^4$); 348 (2.2·10$^4$)

3,8-bis(4'-Aminophenylethinyl)-1,10-phenanthroline (PB$_2$)

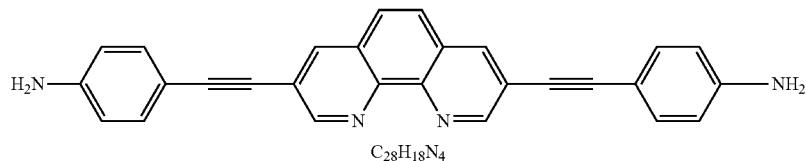

mp: 249-250° C.
$^1$H-NMR (ppm, DMSO-d$_6$):
9.09 (s, 2H phen-2,9), 8.47 (s, 2H phen-4,7), 7.92 (d, 2H phen-5,6), 7.35 (d, 2H Ph), 6.70 (d, 2H Ph), 4.56 (br s, 4H NH$_2$)
$^{13}$C-NMR (ppm, DMSO-d$_6$):
151.3 (phen-C2,9), 150.1 (C—NH$_2$), 137.0 (phen-C4,7), 133.1 (Ph), 127.9 (phen-C5,6), 119.7 (phen-C3,8), 113.6 (Ph), 107.2 (Ph), 96.1 (C≡C), 84.0 (C≡C)
IR (cm$^{-1}$, KBr):
3438 s, 3211 w, 3033 w, 2200 s, 1619 s, 1598 s, 1515 s, 1423 m, 1286 m, 1177 m, 1138 m, 909 w, 830 m, 728 m, 532 w
EI-MS (m/z M$^+$): 410.1 Calculated: 410.153.
UV/Vis spectra (MeOH):
$\lambda_{abs}$=($\epsilon$ in M$^{-1}$ cm$^{-1}$): 280 (4.2·10$^4$); 395 (4.2·10$^4$)

2-(4'-Aminophenylethinyl)-1,10-phenanthroline (P*B)

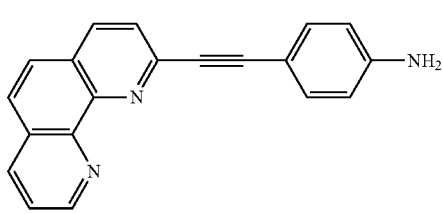

mp: 240-242° C.

¹H-NMR (ppm, CDCl₃):
9.23 (s, 1H phen-9), 8.25 (d, 1H phen-4), 8.19 (d, 1H phen-7), 7.83 (d, 1H phen-3), 7.77 (s, 2H phen-5,6), 7.64 (d, 1H phen-8), 7.49 (d, 2H Ph), 6.66 (d, 2H Ph), 2.00 (br s, 2H $NH_2$)

¹³C-NMR (ppm, CDCl₃):
151.1 (phen-C9), 148.2 (C—$NH_2$), 145.1 (phen-C2), 136.6 (phen-C4), 136.5 (phen-C7), 134.5 (Ph), 127.3 (phen-C5), 127.1 (phen-C6), 126.9 (phen-C3), 123.8 (phen-C8), 115.3 (Ph), 111.9 (Ph), 116.4 (Ph), 92.6 (C≡C), 89.3 (C≡C)

IR (cm⁻¹, KBr):
3439 m, 3295 s, 3199 m, 3035 m, 2194 s, 1618 s, 1603 s, 1582 s, 1549 m, 1518 s, 1482 s, 1445 s, 1386 m, 1307 m, 1154 m, 1082 m, 853 s, 829 s, 741 m, 630 m, 533 m, 473 w

EI-MS (m/z M⁺): 295.2 Calculated: 295.11.

UV/Vis spectra (MeOH):
$\lambda_{abs}$=($\epsilon$ in M⁻¹ cm⁻¹): 233 (3.8·10⁴); 275 (4.7·10⁴); 370 (3.4·10⁴)

Diethylene triamine penta-acetic acid-dianhydride (LH-A)

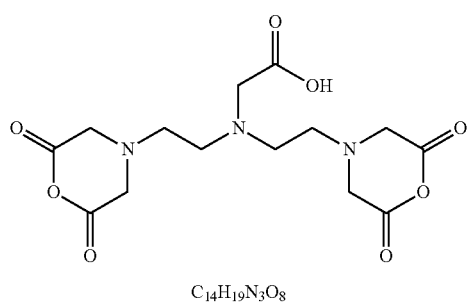

$C_{14}H_{19}N_3O_8$ mp: 176-179° C.

¹H-NMR (ppm, CDCl₃):
3.61 (s, 2H $CH_2$), 3.44 (s, 8H $CH_2$), 3.02 (t, 4H en), 2.89 (t, 4H en)

IR (cm⁻¹, KBr):
3433 m, 2927 m, 2858 w, 1820 s, 1774 s, 1641 s, 1473 m, 1459 m, 1441 m, 1306 m, 1257 m, 1219 m, 1109 s, 958 m, 944 m, 887 w, 606 m, 566 m, 416 m

Antenna ligand $PA_2LH_3$

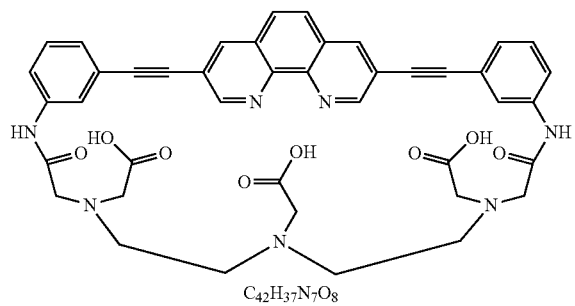

$C_{42}H_{37}N_7O_8$ mp: 195° C. disintegration

¹H-NMR (ppm, DMSO-d₆):
10.33 (br s, OH), 9.23 (d, 2H phen-2,9), 8.78 (d, 2H phen-4,7), 8.12 (s, 2H phen-5,6), 8.09 (s, Ph), 7.76 (m, Ph), 7.37 (m, Ph), 7.11 (d, 2l-1 Ph), 3.58 (s, $CH_2$), 3.50 (s, $CH_2$), 3.47 (s, $CH_2$), 3.10 (t, en), 3.02 (t, en)

IR (cm⁻¹, KBr):
3438 s, 2961 m, 2921 m, 2854 m, 2208 m, 1715 s, 1682 s, 1633 s, 1582 m, 1531 m, 1484 m, 1422 s, 1224 m, 1089 w, 909 m, 792 m, 727 m, 686 m, 527 w

ESI-MS (m/z [M–H]⁻): 766.26256 Calculated: 766.26236.

UV/Vis spectra (H₂O/NH₃ pH=10):
$\lambda_{abs}$ in nm ($\epsilon$ in M⁻¹ cm⁻¹): 205 (2.7·10⁴); 246 (2.6·10⁴); 338 (1.8·10⁴)

Antenna ligand $(PB_2)_2L_2H_6$

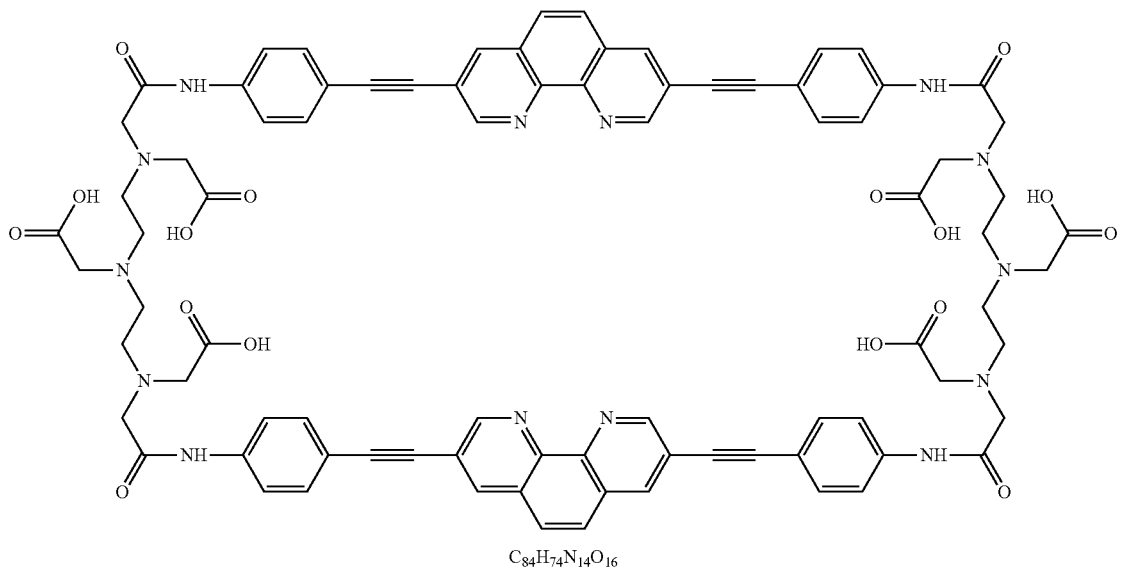

$C_{84}H_{74}N_{14}O_{16}$ mp: >200° C. disintegration
$^1$H-NMR (ppm, DMSO-$d_6$):
10.5 (br s, OH), 8.75 (s, 2H phen-2,9), 8.02 (s, 2H phen-4,7), 7.46 (d, 2H phen-5,6), 7.01
(d, 2H Ph), 6.35 (d, 2H Ph),
IR (cm$^{-1}$, KBr):
3438 s, 2961 m, 2921 m, 2854 m, 2208 w, 1715 s, 1682 s, 1633 s, 1582 m, 1531 m, 1484 m, 1422 m, 1224 m, 1089 w, 909 m, 792 m, 727 m, 686 m
ESI-MS (m/z [2M-2H]$^{2-}$, MeOH, H$_2$O, NH$_3$): 766.26348 Calculated: 766.26308.
UV/Vis spectra (H2O/NH$_3$ pH=10):
$\lambda_{abs}$ in nm ($\epsilon$ in M$^{-1}$ cm$^{-1}$): 282 (3.9·10$^4$); 353 (3.6·10$^4$)

Antenna ligand P*BLH$_4$

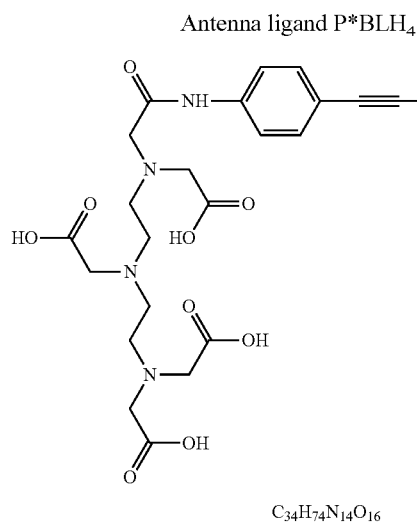

$C_{34}H_{74}N_{14}O_{16}$ mp: starting at 181° C.
$^1$H-NMR (ppm, DMSO-$d_6$):
10.41 (br s, OH), 9.11 (dd), 8.50 (m), 8.02 (s), 7.89 (m), 7.67 (d), 7.64 (d), 3.54 (s, CH$_2$),
3.50 (s, CH$_2$), 3.45 (s, CH$_2$), 3.43 (CH$_2$), 3.09-2.88 (m, en)
FAB-MS (m/z [M+H]$^+$, 3-NBA): 671.2 Calculated: 671.2.
UV/Vis spectra (H$_2$O/NH$_3$ pH=10):
$\lambda_{abs}$ in nm ($\epsilon$ in M$^{-1}$ cm$^{-1}$): 232 (3.6·10$^4$); 311 (3.4·10$^4$); 360 (2.0·10$^4$)

Antenna ligand P*BLH$_3$-EDA

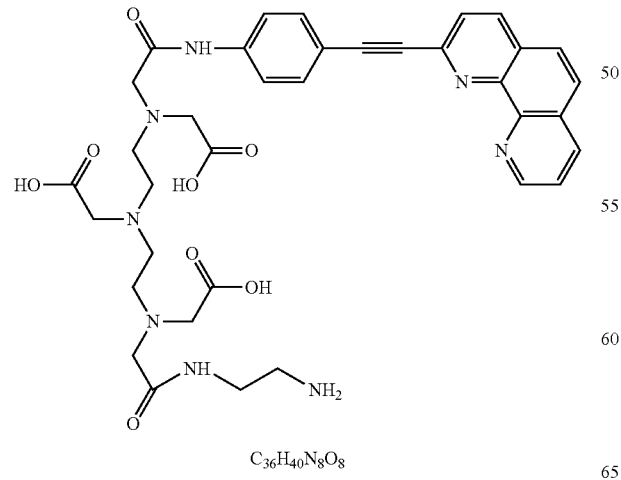

$C_{36}H_{40}N_8O_8$ mp: 190° C.

$^1$H-NMR (ppm, D$_2$O):
An allocation of the signals did not take place.
ESI-MS (m/z [M+H]$^+$, MeOH/H$_2$O+NH$_4$COOH): 713.30462 Calculated: 713.30474.
UV/Vis spectra (H$_2$O):
$\lambda_{abs}$ in nm ($\epsilon$ in M$^{-1}$ cm$^{-1}$): 232 (2.6·10$^4$); 272 (1.8·10$^4$); 310 (2.2·10$^4$); 360 (2.4·10$^4$)

Antenna ligand P*BLH$_3$-SP1

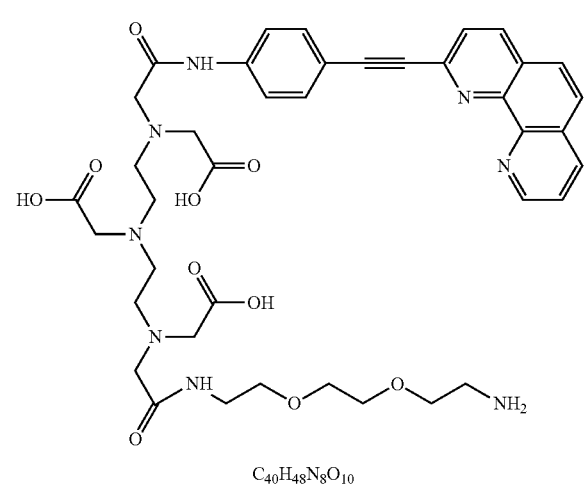

$C_{40}H_{48}N_8O_{10}$ mp: 135° C.
$^1$H-NMR (ppm, D$_2$O):
An allocation of the signals did not take place.
ESI-MS (m/z [M+H]$^+$, MeOH/H$_2$O): 801.35753 Calculated: 801.35662.
UV/Vis spectra (H$_2$O):
$\lambda_{abs}$ in nm ($\epsilon$ in M$^{-1}$ cm$^{-1}$): 232 (2.6·10$^4$); 274 (1.8·10$^4$); 311 (2.2·10$^4$); 359 (2.4·10$^4$)

Indolenine derivative TIPBr$^-$

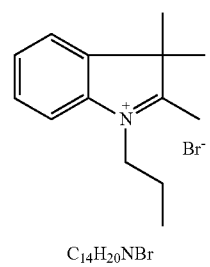

$C_{14}H_{20}NBr$ mp: 158-159° C.
ESI-MS (M$^+$, MeOH): 202.0 Calculated: 202.159.
$^1$H-NMR (ppm, MeOH-$d_4$):
7.89 (m), 7.78 (m), 7.66 (m), 4.51 (t), 2.86 (m), 2.03 (sextet), 1.62 (s), 1.11 (t)

Indolenine derivative TIEOBr⁻

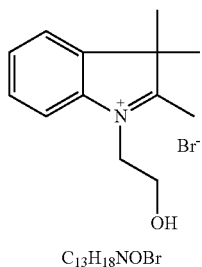

C₁₃H₁₈NOBr mp: 195° C.
¹-H-NMR (ppm, MeOH-d₄):
7.89 (m), 7.78 (m), 7.66 (m), 4.69 (t), 4.06 (q), 3.14 (s), 2.24 (s), 1.63 (s)

Indolenine derivative TIPEBr⁻

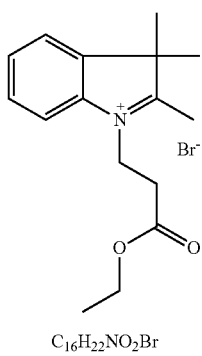

C₁₆H₂₂NO₂Br mp: 130° C.
ESI-MS (M⁺): 260.2 Calculated: 260.165.
¹H-NMR (ppm, CDCl₃):
7.89 (d), 7.58 (m), 4.79 (t), 4.05 (q), 3.14 (s), 2.68 (t), 2.24 (m), 1.62 (s), 1.19 (t)
¹³C-NMR (ppm, CDCl₃):
196.8, 173.2, 142.1, 141.1, 130.7, 130.2, 123.8, 116.5, 61.6, 55.3, 49.4, 23.7, 23.5, 17.4, 14.7

Indolenine derivative TIBEI⁻

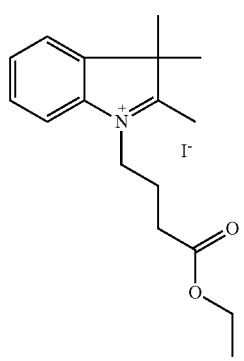

C₁₇H₂₄NO₂I mp: 148° C.
ESI-MS (M⁺): 274.1 Calculated: 274.180.

¹H-NMR (ppm, MeOH-d₄):
8.04 (m), 7.80 (m), 7.65 (m), 4.62 (t), 4.09 (q), 3.14 (s), 2.68 (t), 2.26 (m), 1.65 (s), 1.22 (t)

Polymethine dye ST936

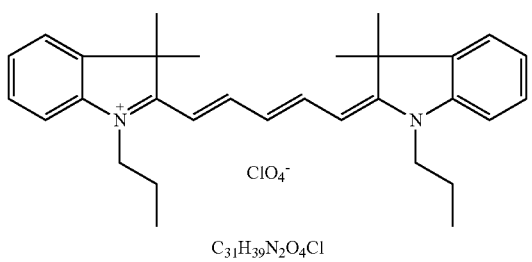

C₃₁H₃₉N₂O₄Cl

ESI-MS (M⁺): 439.3 Calculated: 439.311.
¹H-NMR (ppm, CDCl₃):
8.05 (t), 7.37 (d), 7.35 (d), 7.22 (t), 7.07 (d), 6.64 (t), 6.39 (d), 4.51 (s), 3.99 (t), 3.75 (s),
3.47 (q), 1.74 (s), 1.20 (t), 1.04 (t)
UV/Vis spectra (MeOH):
$\lambda_{abs}$ in nm ($\epsilon$ in $M^{-1}$ $cm^{-1}$): 642 (1.73·10⁵) $\lambda_{em}$ in nm: 668

Polymethine dye Cy5EE

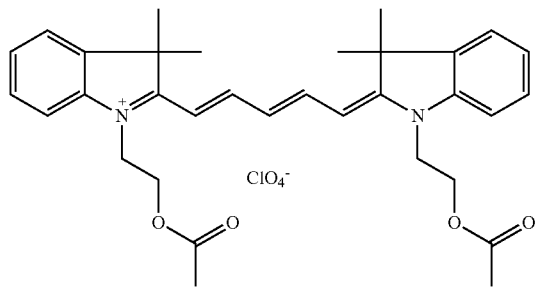

C₃₅H₄₃N₂O₈Cl

ESI-MS (M⁺): 527.2 Calculated:
¹H-NMR (ppm, MeOH-d₄):
8.31 (t), 7.49 (d), 7.43 (t), 7.34 (d), 7.28 (t), 6.64 (t), 6.39 (d), 4.56 (s), 4.51 (m), 4.42 (m),
3.17 (q), 1.86 (s), 1.73 (s), 1.31 (t)
¹H-NMR (ppm, DMSO-d₆):
9.95 (s), 8.39 (t), 7.62 (d), 7.41 (s), 7.25 (d), 6.56 (t), 6.41 (d), 5.32 (s), 4.42 (s), 3.34 (s),
3.06 (dd), 1.82 (s), 1.67 (s), 1.23 (s), 1.19 (t)
¹³C-NMR (ppm, DMSO-d₆):
173.6, 170.1, 154.5, 142.1, 140.9, 128.3, 125.5, 124.7, 122.4, 111.1, 103.6, 60.3, 45.4, 43.2, 27.5, 20.5, 8.5
UV/Vis spectra (MeOH):
$\lambda_{abs}$ in nm ($\epsilon$ in $M^{-1}$ $cm^{-1}$): (3.8·10⁴) $\lambda_{em}$ in nm: 668

Polymethine dye Cy5BE

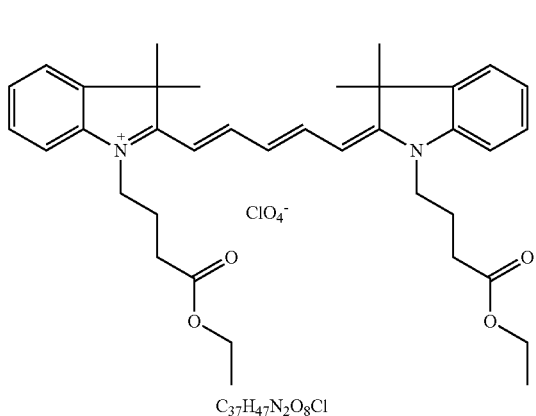

ESI-MS (M$^+$, MeOH): 583.35247 Calculated: 583.35303.
$^1$H-NMR (ppm, MeOH-d$_4$):
8.29 (t), 7.50 (d), 7.43 (t), 7.36 (d), 7.27 (t), 6.63 (t), 6.39 (d), 4.14 (m), 2.85 (t), 2.55 (t),
2.08 (m), 2.03 (s), 1.73 (s), 1.26 (t)
$^{13}$C-NMR (ppm, MeOH-d$_4$):
174.9, 174.5, 155.7, 143.5, 142.6, 129.8, 126.9, 126.3, 123.5, 111.9, 104.4, 63.9, 61.8, 54.4, 44.2, 31.2, 27.9, 23.5, 20.4, 14.5
UV/Vis spectra (MeOH):
$\lambda_{abs}$ in nm ($\epsilon$ in M$^{-1}$ cm$^{-1}$): 642 (1.3·10$^5$) $\lambda_{em}$ in nm: 668

Polymethine dye Cy5'BE

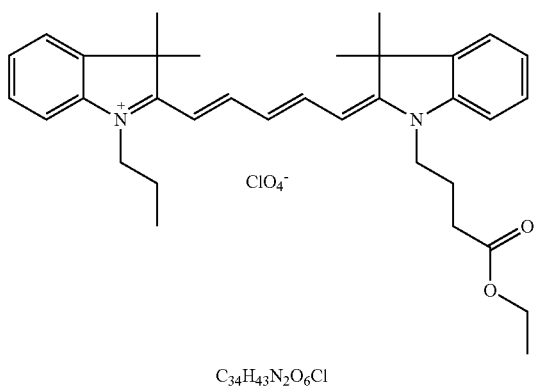

$^1$H-NMR (ppm, MeOH-d$_4$):
An allocation of the signals did not take place.
UV/Vis spectra (MeOH):
$\lambda_{abs}$ in nm ($\epsilon$ in M$^{-1}$ cm$^{-1}$): 643 (7.1·10$^4$) $\lambda_{em}$ in nm: 664

Polymethine dye Cy5BA

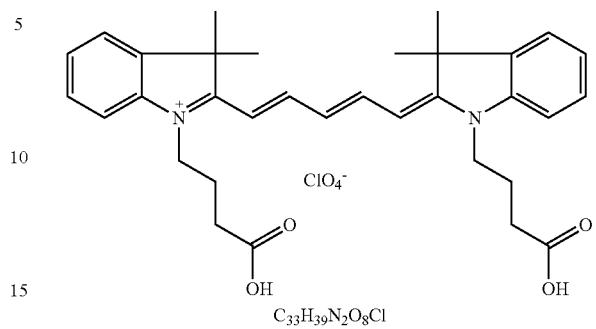

ESI-MS (M$^+$, MeOH): 527.2 Calculated: 527.2909.
$^1$H-NMR (ppm, MeOH-d$_4$):
An allocation of the signals did not take place.
UV/Vis spectra (MeOH): as internal salt
$\lambda_{abs}$ in nm ($\epsilon$ in M$^{-1}$ cm$^{-1}$): 642 (7.9·10$^4$)

Polymethine dye Cy5'BA

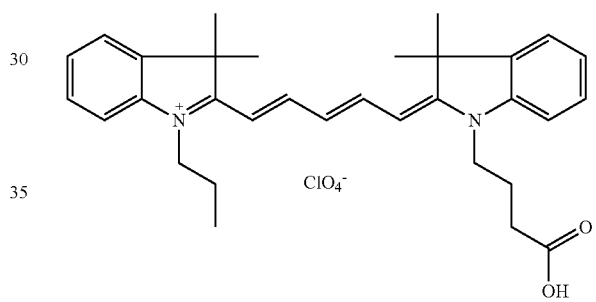

$^1$H-NMR (ppm, DMSO-d$_6$):
An allocation of the signals did not take place.
UV/Vis spectra (MeOH):
$\lambda_{abs}$ in nm ($\epsilon$ in M$^{-1}$ cm$^{-1}$): 643 (1.42·10$^5$) $\lambda_{em}$ in nm: 668

Polymethine dye Cy5E

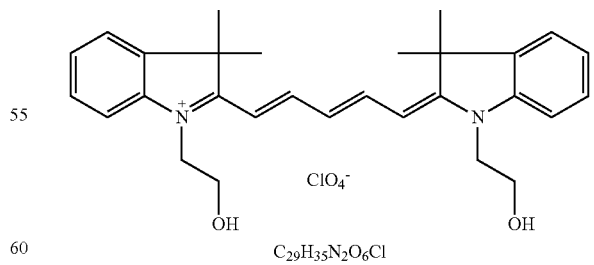

ESI-MS (M$^+$, MeOH): 443.2689 Calculated: 443.2693.
$^1$H-NMR (ppm, DMSO-d$_6$):
8.31 (t), 7.60 (d), 7.38 (s), 7.23 (m), 6.48 (t), 6.33 (d), 5.02 (t), 4.18 (s), 3.76 (d), 3.32 (s)
1.69 (s)

UV/Vis spectra (MeOH):
$\lambda_{abs}$ in nm ($\epsilon$ in M$^{-1}$ cm$^{-1}$): 642 (2.5·10$^5$) $\lambda_{em}$ in nm: 668

Synthesis of the Polymethine Dye Cy5R

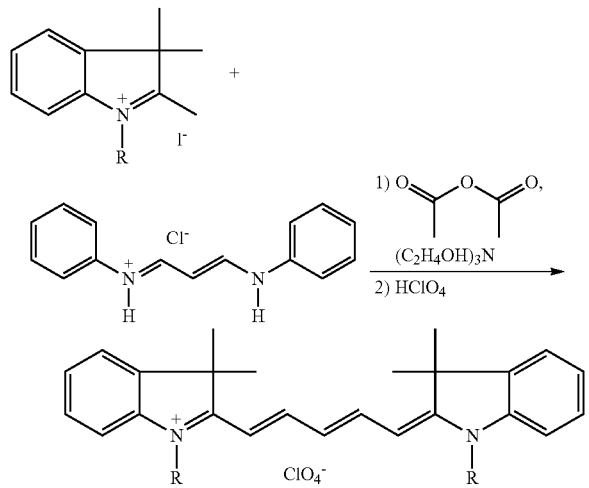

A solution of 20 mmol of the alkylated indolenine and 10 mmol dianilide in 50 mL acetic anhydride is brought to 70° C. and triethanolamine is slowly added dropwise. The dye is precipitated with perchloric acid and suctioned off. In order to recrystallize [it] is dissolved in a little methanol and the solution is added to a 10-fold volume of diethyl ether and left to crystallize at −40° C. (yield approx. 80%).

Indolenine derivative TIPBr⁻

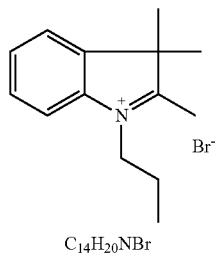

C$_{14}$H$_{20}$NBr mp: 158-159° C.
ESI-MS (M+, MeOH): 202.0 Calculated: 202.159.
1H-NMR (ppm, MeOH-d4):
7.89 (m), 7.78 (m), 7.66 (m), 4.51 (t), 2.86 (m), 2.03 (sextet), 1.62 (s), 1.11 (t)

With respect to the Figures, all fluorescence measurements of the donors [EuP*BL]⁻ and [TbP*BL]⁻ were tracked with a set time delay. The standard settings were as follows:

| For [EuP*BL]⁻: | Excitation wavelength: $\lambda_{exc}$ = 360 nm |
|---|---|
| | Excitation gap: 15 nm   Emission gap: 5 nm |
| | Emission filter: 515 nm |
| | Time window (gt): 4.50 ms |
| | Time delay (dt): 0.07 ms |

| For [TbP*BL]⁻: | Excitation wavelength: $\lambda_{exc}$ = 400 nm |
|---|---|
| | Excitation gap: 15 nm   Emission gap: 10 nm |
| | Emission filter: 430 nm |
| | Time window (gt): 4.60 ms |
| | Time delay (dt): 0.08 ms |

INDEX OF ABBREVIATIONS

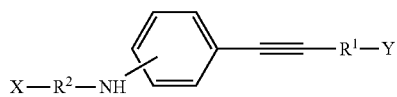

| Abbreviation | n | R$_1$ | R$_2$ |
|---|---|---|---|
| Cy3P | 0 | —C$_3$H$_7$ | —C$_3$H$_7$ |
| Cy5P | 1 | —C$_3$H$_7$ | —C$_3$H$_7$ |
| Cy3BA | 0 | —C$_3$H$_6$COOH | —C$_3$H$_6$COOH |
| Cy5BA | 1 | —C$_3$H$_6$COOH | —C$_3$H$_6$COOH |
| Cy3E | 0 | —C$_2$H$_4$OH | —C$_2$H$_4$OH |
| Cy5E | 1 | —C$_2$H$_4$OH | —C$_2$H$_4$OH |
| Cy3ENCS | 0 | —C$_2$H$_4$OOCPhNCS | —C$_2$H$_4$OOCPhNCS |
| Cy5ENCS | 1 | —C$_2$H$_4$OOCPhNCS | —C$_2$H$_4$OOCPhNCS |
| Cy3'BA | 0 | —C$_3$H$_7$ | —C$_3$H$_6$COOH |
| Cy5'BA | 1 | —C$_3$H$_7$ | —C$_3$H$_6$COOH |
| Cy3'E | 0 | —C$_3$H$_7$ | —C$_2$H$_4$OH |
| Cy5'E | 1 | —C$_3$H$_7$ | —C$_2$H$_4$OH |
| Cy3'ENCS | 0 | —C$_3$H$_7$ | —C$_2$H$_4$OOCPhNCS |
| Cy5'ENCS | 1 | —C$_3$H$_7$ | —C$_2$H$_4$OOCPhNCS |

CDI N,N' carbonyl diimide azole
CDD N-ethyl-N'-(3-diamethyl aminopropyl)-carbodiimide
EDA Ethylene diamine
FIA Fluorescence immunoassay
phen Phenanthroline
DMF-TEA Diamethylformamide triethanolamine

The invention claimed is:

1. An ethinyl aniline compound for determination of biomolecules according to the following formula:

$$X-R^2-NH-\underset{}{\bigcirc}-C\equiv C-R^1-Y$$

where

R$^1$ is an antenna function, the antenna function is one of 1,10-phenanthroline (1), fluorene (2), acetophenone (3), benzophenone (4), fluorenone (5), xanthenone (6), azaxanthone (7), anthraquinone (8), acridone (9), quinoline (10) and coumarin (11)

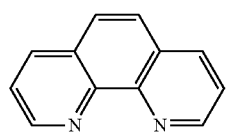

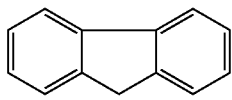

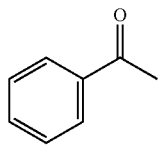

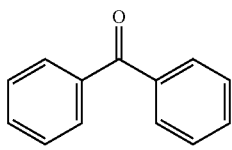

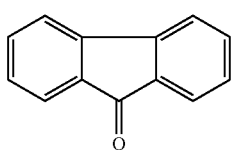

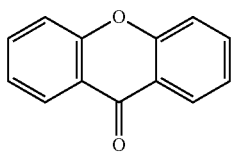

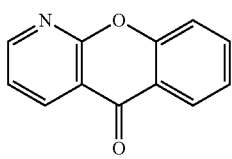

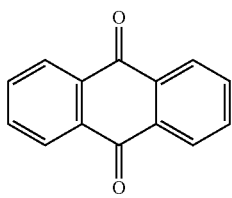

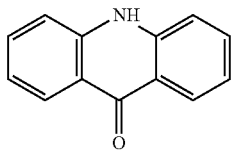

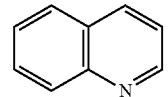

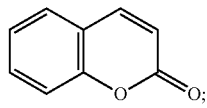

$R^2$ is a chelate forming agent, containing a coordinated lanthanide (III) ion;

X is —OH or a group with affinity for a biomolecule, bonded to a carboxylate group of the chelate forming agent by means of an amide bond; and Y is —H or a group with affinity for the biomolecule, coupled to the antenna function.

2. The compound according to claim 1, in which a) the chelate forming agent with a lanthanide (III) ion is one of diethylene triamine penta-acetic acid (12, where n=1), triethylenetetraamine hexaacetic acid (TTHA) (12, where n=2) and the TTHA isomer [nitrilotris(ethylenenitrilo)] hexaacetic acid (NTTHA) (13)

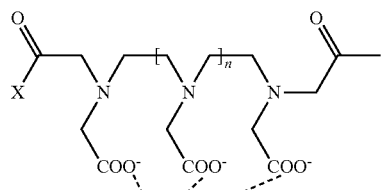

whereby the TTHA derivates can contain a second ethinyl aniline with an antenna function so that three carboxylate groups are available for complex formation;

b) X comprises one of —NH(CH$_2$)$_2$NH$_2$, —NH(CH$_2$)$_2$PhNH$_2$, NH(CH$_2$)$_2$PhNCS, —NH(CH$_2$)$_n$NH(C$_3$N$_3$Cl$_2$) with n=2 to 6 and —NH(CH$_2$)$_2$O(CH$_2$)$_2$O(CH$_2$)$_2$NH$_2$;

c) Y comprises one of the following groups with affinity:

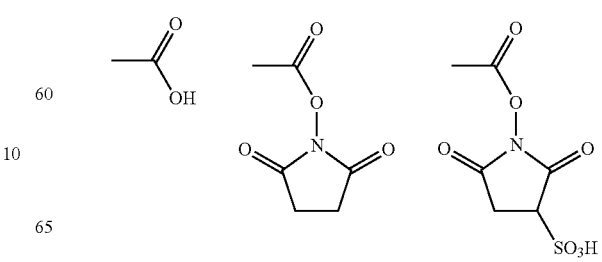

-continued

—NCS  —NH₂  and

[structures: chloroacetone; NCS; NH₂; iodoacetamide —NH-C(O)-CH₂-I]

and d) the lanthanide (III) ion is one of Eu³⁺, Tb³⁺, Dy³⁺ and Sm³⁺.

3. The compound of claim 1 wherein the antenna function is 1,10-phenanthroline.

4. A method of manufacturing 2-(4'-aminophenyl ethinyl)-1,10-phenanthroline comprising reacting 2-chloro-1,10-phenanthroline with p-ethinyl aniline.

5. The compound of claim 1 wherein the chelate forming agent is diethylene triamine penta-acetic acid or dissociation stages of the diethylene triamine penta-acetic acid.

6. The compound of claim 1 wherein the antenna function is 1,10-phenanthroline and the chelate forming agent is diethylene triamine penta-acetic acid or dissociation stages of the diethylene triamine penta-acetic acid.

7. The compound of claim 6 wherein the lanthanide (III) ion is Eu³⁺ and the compound optionally includes a tetrabutyl ammonium counterion.

8. The compound of claim 6 wherein the lanthanide (III) ion is Tb³⁺ and the compound optionally includes a tetrabutyl ammonium counterion.

9. The compound of claim 6 wherein X is —NH(CH₂)₂NH₂ or —NH(CH₂)₂O(CH₂)₂O(CH₂)₂NH₂.

10. The compound of claim 9 wherein the lanthanide (III) ion is Eu³⁺.

11. A fluorometric analytical method for qualitative detection and quantitative determination of a biomolecule in a sample, comprising:
   contacting the sample with the ethinyl aniline compound of claim 1, wherein the ethinyl aniline compound is bound covalently to the biomolecule via a linker reaction, wherein the biomolecule is one of peptides, proteins, oligonucleotides, nucleic acids, oligosaccharides, polysaccharides, glycoproteins, phospholipids, low-molecular substrates of enzymes and low-molecular ligands of proteins; and
   detecting fluorescence, thereby qualitatively detecting and quantitatively determining the biomolecule in the sample.

12. The fluorometric analytical method of claim 11, wherein detecting fluorescence comprises measuring directly the fluorescence of the lanthanide (III).

13. A fluorometric analytical method for qualitative detection and quantitative determination of a first biomolecule in a sample, comprising:
   contacting the sample with the ethinyl aniline compound of claim 1, wherein the ethinyl aniline compound is bound covalently to the first biomolecule via a linker reaction;
   adding to the sample an organic dye from the class of polymethine dyes bound to a second biomolecule;
   exciting the ethinyl aniline compound; and
   detecting the level of fluorescence resonance energy transfer,
wherein the first biomolecule and second biomolecule are each one of peptides, proteins, oligonucleotides, nucleic acids, oligosaccharides, polysaccharides, glycoproteins, phospholipids, low-molecular substrates of enzymes and low-molecular ligands of proteins, wherein the energy transferred from the ethinyl aniline compound to the organic dye is determined by measuring the fluorescent emission of the organic dye and thereby qualitatively detecting and quantitatively determining the first biomolecule in the sample.

14. A fluorescence resonance energy transfer bioassay kit comprising:
   the ethinyl aniline compound of claim 1;
   N,N'-carbonyl diimide azole or N-ethyl-N'-(3-diaminopropyl)-carbodiimide (CDD) and triethanolamine/HCl buffer for marking;
   Eu (III) chloride as 10⁻³ mol/l solution in water; and
   Cy5 dye with acidic function as a solid,
wherein the ethinyl aniline compound has an excitation wavelength $\lambda_{exc}$ of 360 nm and a detection wavelength $\lambda_{em}$ of 665 nm.

15. The fluorescence resonance energy transfer bioassay kit of claim 14, wherein the Cy5 dye with acidic function is one of Cy5ENCS

[structure of Cy5ENCS]

Cy5BE

[structure of Cy5BE]

Cy5EE

[structure of Cy5EE]

and Cy5'BE
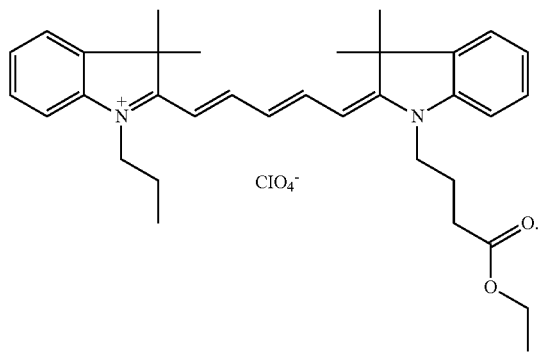
16. The fluorescence resonance energy transfer bioassay kit of claim 14, wherein the ethinyl aniline compound is
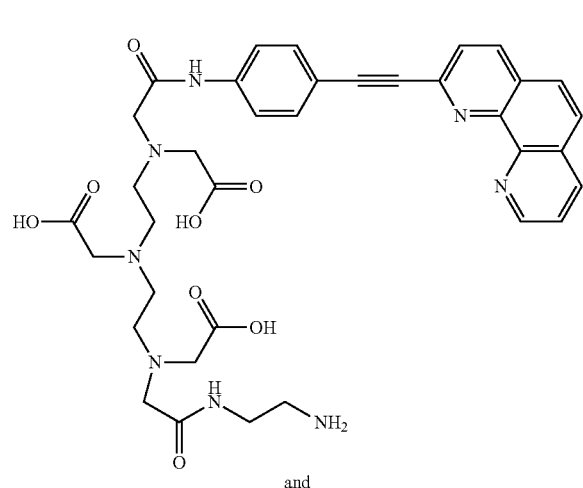
and
the Cy5 dye with acidic function is one of Cy5P
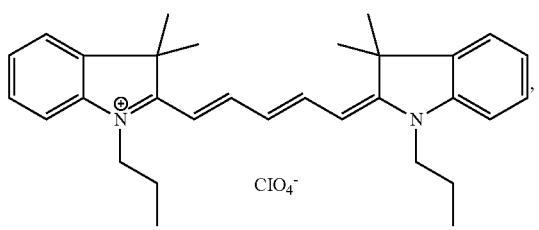
Cy5BA
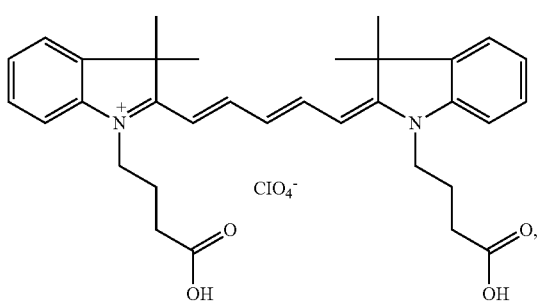
Cy5E
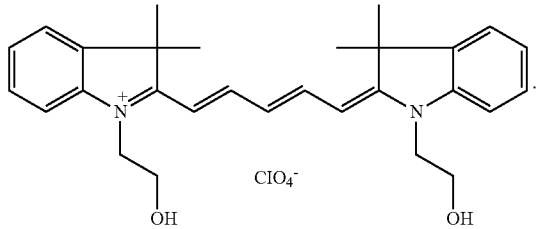
and Cy5ENCS
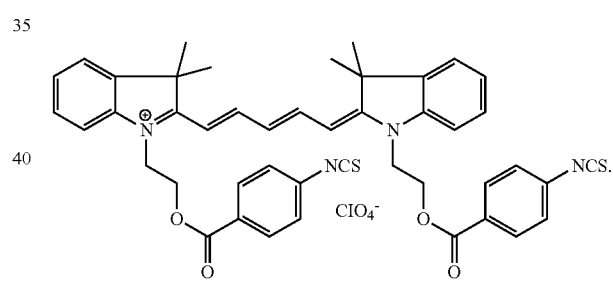
17. The fluorescence resonance energy transfer bioassay kit of claim 14, wherein the Cy5 dye is bound to a secondary antibody, protein A or protein G.
* * * * *